(12) United States Patent
Kabiri et al.

(10) Patent No.: US 11,692,938 B2
(45) Date of Patent: Jul. 4, 2023

(54) OPTICAL NANOSTRUCTURE REJECTER FOR AN INTEGRATED DEVICE AND RELATED METHODS

(71) Applicant: Quantum-Si Incorporated, Guilford, CT (US)

(72) Inventors: Ali Kabiri, Guilford, CT (US); Bing Shen, Branford, CT (US); James Beach, Austin, TX (US); Kyle Preston, Guilford, CT (US); Gerard Schmid, Guilford, CT (US)

(73) Assignee: Quantum-Si Incorporated, Guilford, CT (US)

( * ) Notice: Subject to any disclaimer, the term of this patent is extended or adjusted under 35 U.S.C. 154(b) by 153 days.

(21) Appl. No.: 16/905,350

(22) Filed: Jun. 18, 2020

(65) Prior Publication Data

US 2020/0400568 A1    Dec. 24, 2020

Related U.S. Application Data

(60) Provisional application No. 62/863,635, filed on Jun. 19, 2019.

(51) Int. Cl.
    *G01N 21/64*     (2006.01)
    *H01L 27/146*    (2006.01)

(52) U.S. Cl.
    CPC ..... *G01N 21/6428* (2013.01); *G01N 21/6402* (2013.01); *G01N 21/6408* (2013.01);
    (Continued)

(58) Field of Classification Search
    CPC .... G12Q 1/6869; G02B 6/005; G02B 6/4215; G02B 6/1225; G02B 5/203;
    (Continued)

(56) References Cited

U.S. PATENT DOCUMENTS

| | | |
|---|---|---|
| 5,961,924 A | 10/1999 | Reichert et al. |
| 6,787,308 B2 | 9/2004 | Balasubramanian et al. |

(Continued)

FOREIGN PATENT DOCUMENTS

| | | |
|---|---|---|
| EP | 2 884 261 | 6/2015 |
| WO | 2011/153962 | 12/2011 |

OTHER PUBLICATIONS

International Search Report and Written Opinion for International Application No. PCT/US2020/038415 dated Oct. 8, 2020 (R0708.70061WOOO).

(Continued)

*Primary Examiner* — John R Lee
(74) *Attorney, Agent, or Firm* — Wolf, Greenfield & Sacks, P.C.

(57) ABSTRACT

Apparatus and methods relating to photonic bandgap optical nanostructures are described. Such optical nanostructures may exhibit prohibited photonic bandgaps or allowed photonic bands, and may be used to reject (e.g., block or attenuate) radiation at a first wavelength while allowing transmission of radiation at a second wavelength. Examples of photonic bandgap optical nanostructures includes periodic and quasi-periodic structures, with periodicity or quasi-periodicity in one, two, or three dimensions and structural variations in at least two dimensions. Such photonic bandgap optical nanostructures may be formed in integrated devices that include photodiodes and CMOS circuitry arranged to analyze radiation received by the photodiodes.

30 Claims, 21 Drawing Sheets

(52) U.S. Cl.
CPC .. *H01L 27/14625* (2013.01); *H01L 27/14685* (2013.01); *G01N 2021/6439* (2013.01); *G01N 2201/063* (2013.01); *G01N 2201/06113* (2013.01)

(58) Field of Classification Search
CPC ......... H01L 27/14643; H01L 27/14685; H01L 27/14625; G01B 1/005; G01N 2021/7786; G01N 21/7706; G01N 21/648; G01N 21/6454; G01N 2201/063; G01N 2201/06113; G01N 2021/6439; G01N 21/6408; G01N 21/6402; G01N 21/6428
See application file for complete search history.

(56) References Cited

U.S. PATENT DOCUMENTS

| | | | |
|---|---|---|---|
| 6,917,726 B2 | 7/2005 | Levene et al. | |
| 7,175,811 B2 | 2/2007 | Bach et al. | |
| 7,426,322 B2 | 9/2008 | Hyde | |
| 7,738,086 B2 | 6/2010 | Shepard et al. | |
| 7,820,983 B2 | 10/2010 | Lundquist et al. | |
| 7,834,329 B2 | 11/2010 | Lundquist et al. | |
| 7,838,847 B2 | 11/2010 | Lundquist et al. | |
| 8,053,742 B2 | 11/2011 | Lundquist et al. | |
| 8,207,509 B2 | 6/2012 | Lundquist et al. | |
| 8,274,040 B2 | 9/2012 | Zhong et al. | |
| 8,278,728 B2 | 10/2012 | Murshid | |
| 8,465,699 B2 | 6/2013 | Fehr et al. | |
| 8,471,219 B2 | 6/2013 | Lundquist et al. | |
| 8,471,230 B2 | 6/2013 | Zhong et al. | |
| 8,502,169 B2 | 8/2013 | Rigneault et al. | |
| 8,618,507 B1 | 12/2013 | Lundquist et al. | |
| 9,029,802 B2 | 5/2015 | Lundquist et al. | |
| 9,146,235 B2* | 9/2015 | Van Dorpe | G01N 21/648 |
| 9,157,864 B2 | 10/2015 | Fehr et al. | |
| 9,222,123 B2 | 12/2015 | Zhong et al. | |
| 9,222,133 B2 | 12/2015 | Lundquist et al. | |
| 9,223,084 B2 | 12/2015 | Grot et al. | |
| 9,372,308 B1 | 6/2016 | Saxena et al. | |
| 9,587,276 B2 | 3/2017 | Lundquist et al. | |
| 9,606,060 B2 | 3/2017 | Chen et al. | |
| 9,658,161 B2 | 5/2017 | Saxena et al. | |
| 9,666,748 B2 | 5/2017 | Leobandung | |
| 9,719,138 B2 | 8/2017 | Zhong et al. | |
| 9,765,395 B2 | 9/2017 | Goldsmith | |
| 9,921,157 B2* | 3/2018 | Rothberg | G01N 21/6408 |
| 9,946,017 B2 | 4/2018 | Saxena et al. | |
| 9,983,135 B2* | 5/2018 | Rothberg | G01N 21/7743 |
| 10,018,764 B2 | 7/2018 | Grot et al. | |
| 10,090,429 B2 | 10/2018 | Leobandung | |
| 10,138,515 B2 | 11/2018 | Fehr et al. | |
| 10,280,457 B2 | 5/2019 | Zhong et al. | |
| 10,310,178 B2 | 6/2019 | Saxena et al. | |
| 10,487,356 B2 | 11/2019 | Lundquist et al. | |
| 10,578,788 B2 | 3/2020 | Grot et al. | |
| 10,655,172 B2 | 5/2020 | Rank et al. | |
| 10,724,090 B2 | 7/2020 | McCaffrey et al. | |
| 2002/0182716 A1 | 12/2002 | Weisbuch et al. | |
| 2003/0174992 A1 | 9/2003 | Levene et al. | |
| 2010/0065726 A1 | 3/2010 | Zhong et al. | |
| 2012/0021525 A1 | 1/2012 | Fehr et al. | |
| 2012/0257204 A1 | 10/2012 | Walters | |
| 2013/0116153 A1 | 5/2013 | Bowen et al. | |
| 2015/0141267 A1* | 5/2015 | Rothberg | G01N 21/6486 250/208.2 |
| 2015/0168392 A1* | 6/2015 | Van Dorpe | G01N 15/1456 435/7.1 |
| 2015/0177150 A1* | 6/2015 | Rothberg | G01N 21/648 506/38 |
| 2016/0355869 A1* | 12/2016 | Blair | G01N 21/648 |
| 2017/0146479 A1 | 5/2017 | Levine et al. | |
| 2018/0059020 A1* | 3/2018 | Strangi | G01N 21/7743 |
| 2018/0088052 A1* | 3/2018 | Rothberg | G01N 21/7743 |
| 2018/0120229 A1* | 5/2018 | Rothberg | C12Q 1/6874 |
| 2019/0292590 A1 | 9/2019 | Zhong et al. | |
| 2020/0400568 A1* | 12/2020 | Kabiri | G01N 21/6408 |

OTHER PUBLICATIONS

Hale, Fibre Optic Sensors using Adiabatically Tapered Single Mode Fibres. Dissertation submitted to the University of Cambridge. Feb. 1994. 209 pages.

Mogensen et al., A Microfluidic Device with an Integrated Waveguide Beam Splitter for Velocity Measurements of Flowing Particles by Fourier Transformation. Analytical Chemistry. 2003 Sep. 15;75(18):4931-4936.

Taitt et al., Evanescent wave fluorescence biosensors. Biosens Bioelectron. Jun. 2005;20(12):2470-87. Epub Dec. 8, 2004.

* cited by examiner

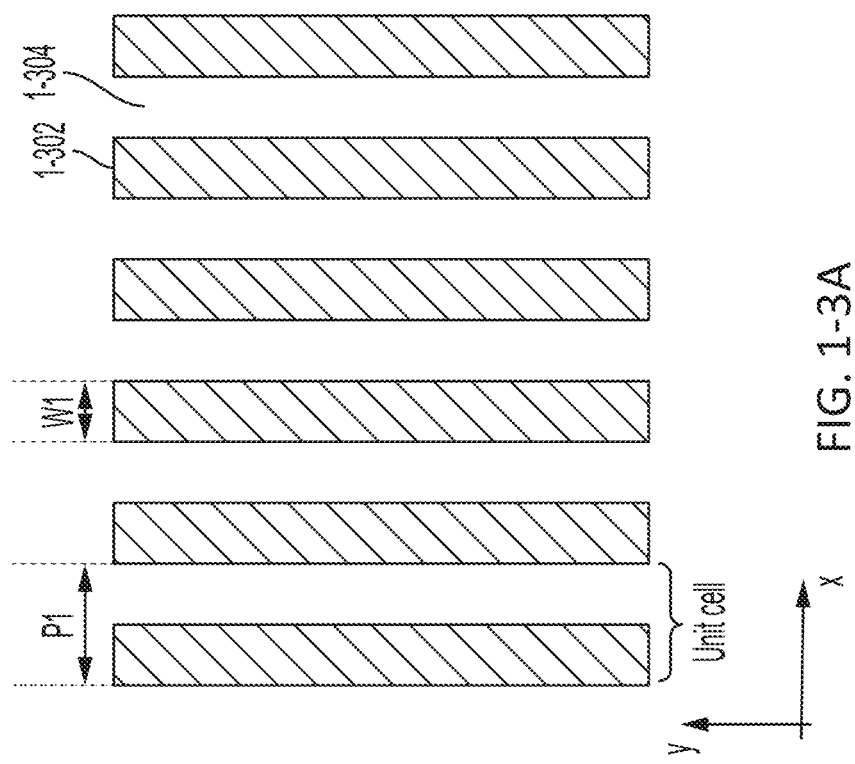
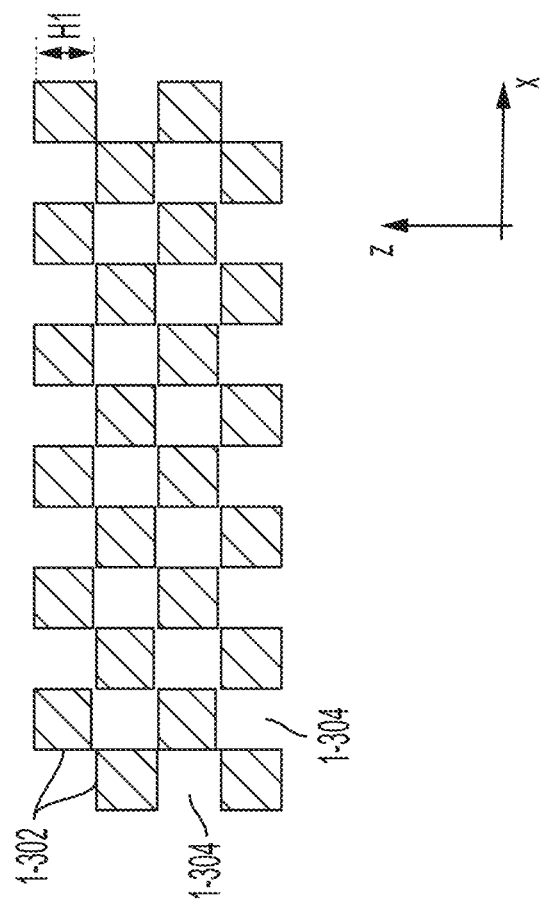
FIG. 1-3A
FIG. 1-3B

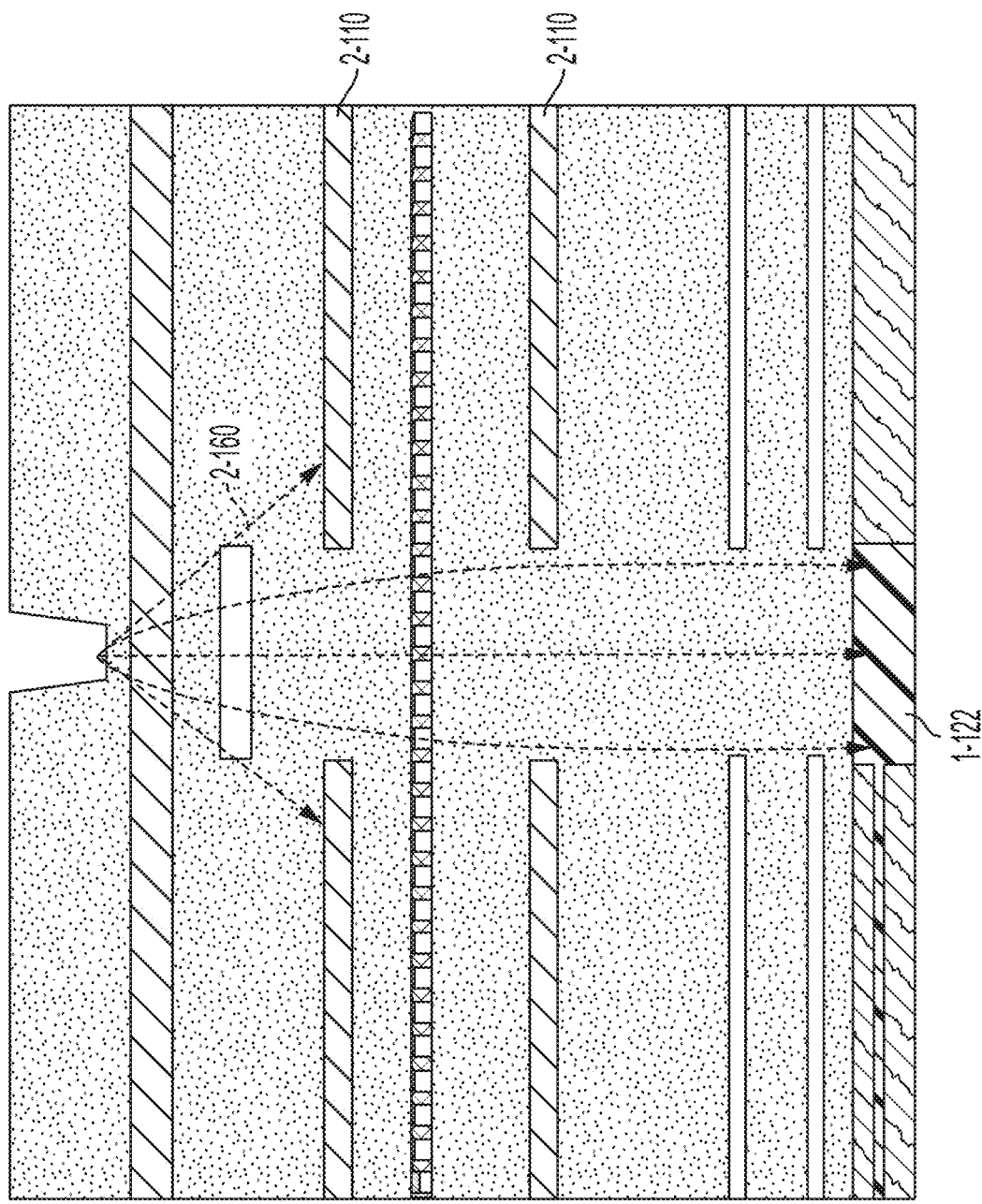

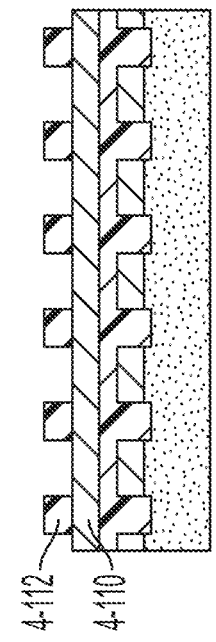
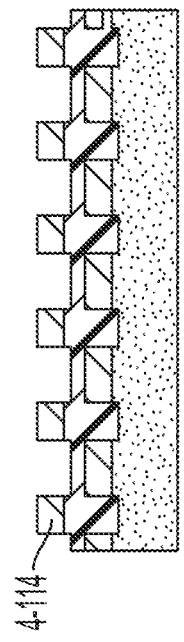
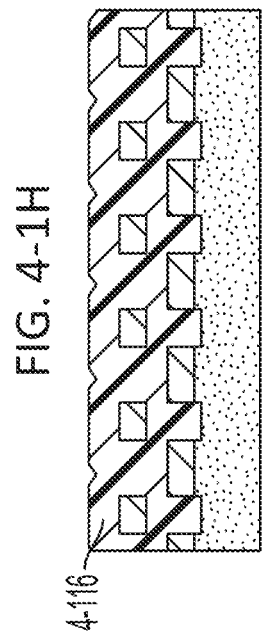
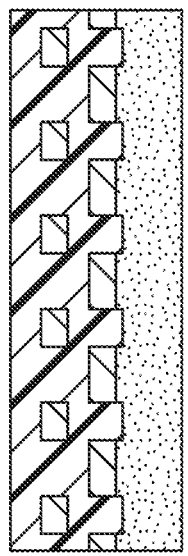
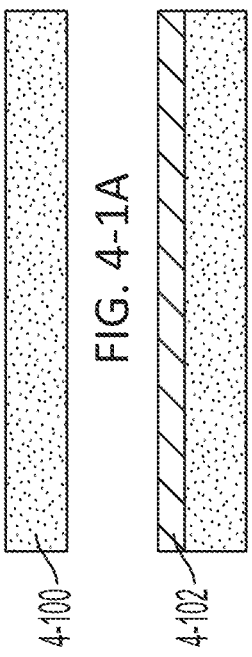
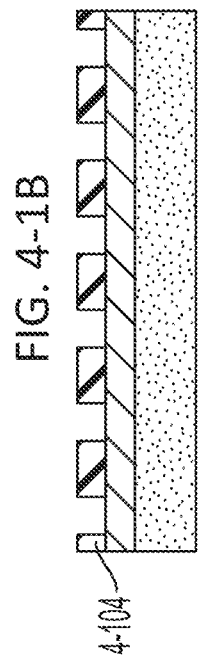
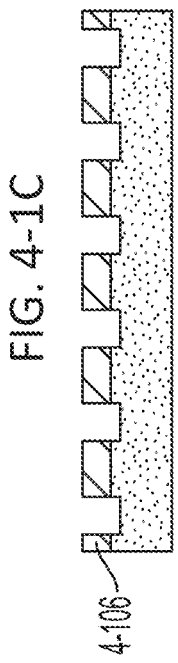
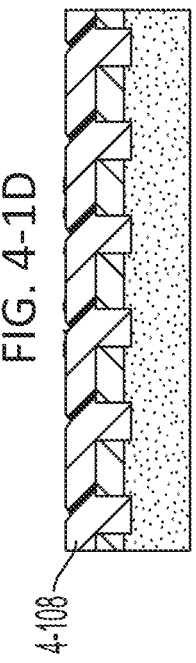
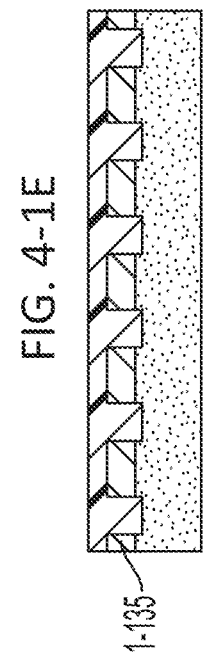

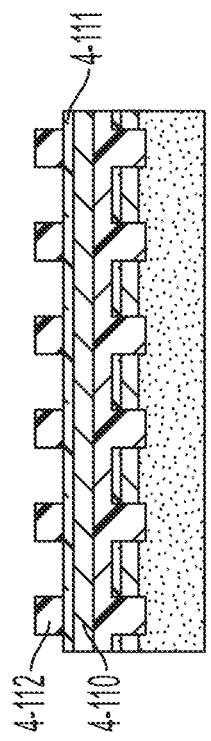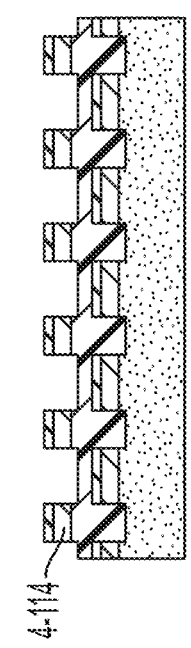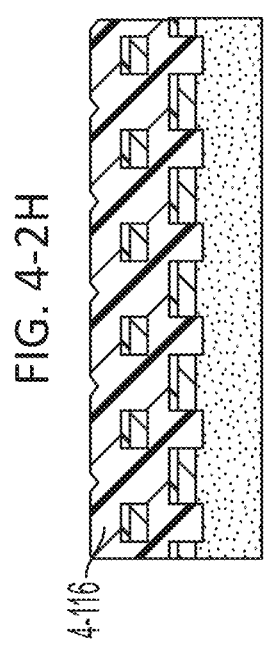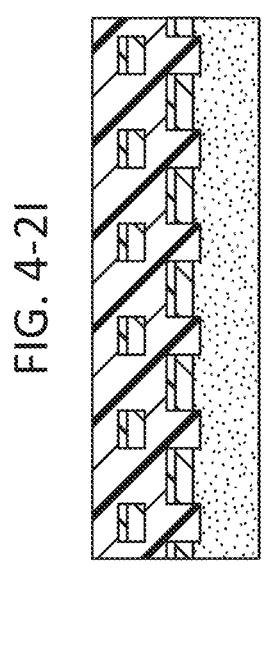
FIG. 4-2G  FIG. 4-2H  FIG. 4-2I  FIG. 4-2J
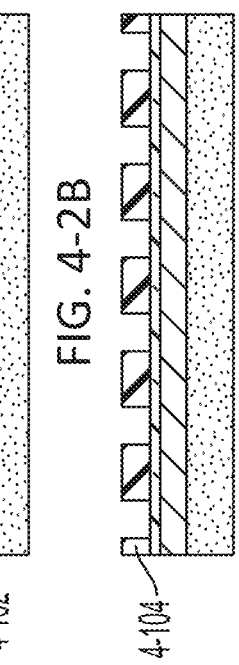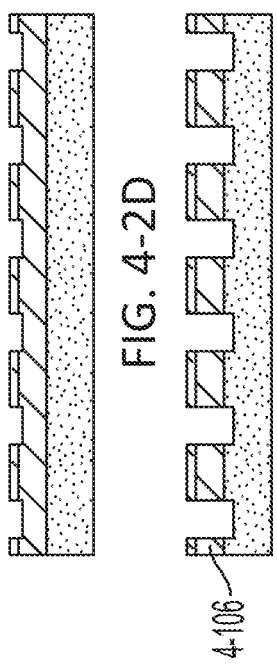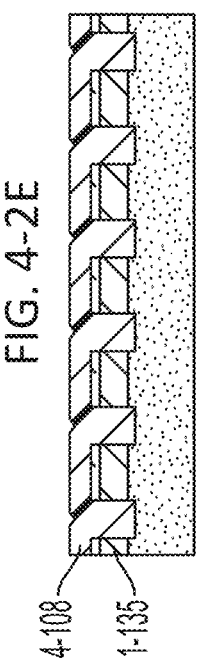
FIG. 4-2A  FIG. 4-2B  FIG. 4-2C  FIG. 4-2D  FIG. 4-2E  FIG. 4-2F

OPTICAL NANOSTRUCTURE REJECTER FOR AN INTEGRATED DEVICE AND RELATED METHODS

CROSS-REFERENCE TO RELATED APPLICATIONS

This application claims priority under 35 U.S.C. § 119(e) to U.S. Provisional Patent Application Ser. No. 62/863,635, entitled "OPTICAL NANOSTRUCTURE REJECTER FOR AN INTEGRATED DEVICE AND RELATED METHODS," filed on Jun. 19, 2019, which is hereby incorporated herein by reference in its entirety.

FIELD

The present application relates to reducing, with an optical nanostructure, unwanted radiation in an integrated device.

BACKGROUND

In the area of instrumentation that is used for analysis of samples, microfabricated chips may be used to analyze a large number of analytes or specimens (contained within one or more samples) in parallel. In some cases, optical excitation radiation is delivered to a plurality of discrete sites on a chip at which separate analyses are performed. The excitation radiation may excite a specimen at each site, a fluorophore attached to the specimen, or a fluorophore involved in an interaction with the specimen. In response to the excitation, radiation may be emitted from a site and the emitted radiation may be detected by a sensor. Information obtained from the emitted radiation for a site, or lack of emitted radiation, can be used to determine a characteristic of the specimen at that site.

SUMMARY

Apparatus and methods relating to photonic bandgap optical nanostructures are described. Such optical nanostructures may exhibit prohibited photonic bandgaps or allowed photonic bandgaps, and may be used to reject radiation (e.g., block or attenuate a majority of the radiation) at a first wavelength while allowing transmission of radiation at a second wavelength. Examples of photonic bandgap optical nanostructures includes periodic and quasi-periodic structures, with structural variations in two or three dimension and periodicity or quasi-periodicity in one, two, or three dimensions. Such photonic bandgap optical nanostructures may be formed in integrated devices that include optical sensors, such as photodiodes, CCD photodiode arrays, CMOS photodiode arrays, image sensor arrays, fluorescent sensor arrays, etc. In an example embodiment, a photonic bandgap optical nanostructure can be used in connection with instruments for analyzing specimens, where optical detection is used to analyze the radiation emitted by a specimen in response to optical excitation delivered to the specimen. Photonic bandgap optical nanostructures may be useful in these contexts to reduce certain radiation in one or more wavelength bands that contribute to background noise while allowing transmission of radiation in a wavelength band that contains useful signal, thereby improving signal-to-noise ratio.

Some embodiments relate to an integrated device comprising a substrate having a first surface, and a plurality of pixels formed on the substrate. At least some of the plurality of pixels comprises a reaction chamber configured to receive a sample; a sensor configured to detect radiation emitted from the reaction chamber; a waveguide configured to couple excitation radiation to the reaction chamber; and an optical nanostructure disposed between the waveguide and the sensor. The optical nanostructure is patterned to include structural variations in a plane parallel to the first surface of the substrate and rejects at least a portion of the excitation radiation incident on the optical nanostructure in a direction normal to the first surface.

In some embodiments, the structural variations are periodic or quasi-periodic at least in one dimension in the plane.

In some embodiments, the optical nanostructure exhibits a photonic bandgap.

In some embodiments, the structural variations are periodic or quasi-periodic in two dimensions in the plane.

In some embodiments, the structural variations exhibit a periodicity between 150 nm and 500 nm.

In some embodiments, the optical nanostructure has no missing or significantly different periodic component within the structural variations.

In some embodiments, the optical nanostructure comprises a first plurality of discrete regions of a dielectric material having a first refractive index.

In some embodiments, the first plurality of discrete regions of the dielectric material exhibit a width, in the plane, between 100 nm and 300 nm.

In some embodiments, the optical nanostructure comprises a second plurality of discrete regions of the dielectric material, the first and second discrete regions of the dielectric material being spaced from each other along a direction perpendicular to the first surface of the substrate.

In some embodiments, the first and second discrete regions of dielectric material are staggered from each other along the direction parallel to the plane.

In some embodiments, the first plurality of discrete regions of the dielectric material are separated by regions of a material having a second refractive index different than the first refractive index.

In some embodiments, the first plurality of discrete regions of the dielectric material extend in a direction perpendicular to the plane.

In some embodiments, the first plurality of discrete regions of the dielectric material exhibit a height, along the direction perpendicular to the first surface of the substrate, between 100 nm and 300 nm.

In some embodiments, the integrated device further comprises an iris disposed between the reaction chamber and the sensor.

In some embodiments, the integrated device further comprises an optical element disposed between the reaction chamber and the sensor that increases a concentration of the emission radiation onto the sensor.

In some embodiments, the optical element comprises a disk of dielectric material having, for a same wavelength of the emission radiation, a first index of refraction that is different from a second index of refraction for material surrounding the disk.

Some embodiments relate to a method of operating an integrated device. The method comprises coupling, from a waveguide formed on a substrate, excitation radiation to a reaction chamber formed adjacent to the waveguide, the excitation radiation having a first wavelength; passing emission radiation from the reaction chamber through an optical nanostructure to a sensor, wherein the optical nanostructure is patterned to include structural variations in a plane parallel to a first surface of the substrate, and wherein the emission radiation has a second wavelength different than the first wavelength and is generated in response to excitation of at least one emitter in the reaction chamber by the excitation radiation; and rejecting at least a portion of the excitation radiation with the optical nanostructure.

In some embodiments, the method further comprises detecting at least a portion of the emission radiation which passes through the optical nanostructure with a sensor formed on the substrate.

In some embodiments, rejecting a portion of the excitation radiation comprises causing the portion of the excitation radiation to reflect from the optical nanostructure.

In some embodiments, the first wavelength is within a photonic bandgap of the optical nanostructure.

In some embodiments, the second wavelength is outside the photonic bandgap of the optical nanostructure.

In some embodiments, the structural variations are periodic or quasi-periodic at least in one dimension in the plane.

In some embodiments, the structural variations are periodic or quasi-periodic in two dimensions in the plane.

In some embodiments, the method further comprises passing the emission radiation from the reaction chamber through an iris.

In some embodiments, the method further comprises rejecting the excitation radiation with the iris.

In some embodiments, the method further comprises concentrating the emission radiation with a dielectric disk located between the reaction chamber and optical nanostructure.

Some embodiments relate to a method for fabricating an integrated device. The method comprises forming, on a substrate having a first surface, a plurality of pixels such that at least some of the plurality of pixels comprises a reaction chamber and a sensor; forming a waveguide in the at least some of the plurality of pixels; and forming an optical nanostructure in the at least some of the plurality of pixels between the waveguide and the sensor. Forming the optical nanostructure comprises patterning a first dielectric material to include structural variations in a plane parallel to the first surface of the substrate.

In some embodiments, patterning a first dielectric material comprises forming periodic or quasi-periodic patterns in the first dielectric material.

In some embodiments, patterning the first dielectric material to include structural variations comprises etching the first dielectric material to form voids in the first dielectric material.

In some embodiments, the method further comprises filling the voids with a second dielectric material different than the first dielectric material.

In some embodiments, the method further comprises performing a planarization process step prior to forming the waveguide in the at least some of the plurality of pixels.

In some embodiments, forming the waveguide comprises forming the waveguide using a same material as the first dielectric material.

The foregoing and other aspects, implementations, acts, functionalities, features and, embodiments of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

FIG. 1-2 is a plot illustrating the spectral response of an example optical nanostructure, according to some embodiments.

FIG. 1-3A is a top view illustrating an example of an optical nanostructure that is periodic in one dimension (x direction) and has structural variations in at least two dimensions (x and z), according to some embodiments.

FIG. 1-3B is an elevation view illustrating an example of an optical nanostructure including multiple layers, according to some embodiments.

FIG. 1-3C is a top view illustrating an example of an optical nanostructure that is periodic in two dimensions, according to some embodiments.

FIG. 1-3D is a perspective view illustrating another example of an optical nanostructure that is periodic in two dimensions, according to some embodiments.

FIG. 1-3E is a top view illustrating an example of an optical nanostructure that is quasi-periodic in one dimension, according to some embodiments.

FIG. 1-3F is a top view illustrating an example of an optical nanostructure that is quasi-periodic in two dimensions, according to some embodiments.

FIG. 1-4A is a plot illustrating an example electric field of excitation radiation in the structure of FIG. 1-1, the electric field being computed at a first wavelength, according to some embodiments.

FIG. 1-4B is a plot illustrating an example electric field of emission radiation that may emit from a reaction chamber in the structure of FIG. 1-1, the electric field being computed at a second wavelength, according to some embodiments.

FIG. 1-5 is a plot illustrating optical rejection as a function of angle of incidence for two types of optical nanostructures, according to some embodiments.

FIG. 2-1 is a schematic diagram illustrating another example of structure at a pixel of an integrated device, according to some embodiments.

FIG. 2-2 depicts the structure of FIG. 2-1 and includes rays of emission radiation, according to some embodiments.

FIG. 2-3 is a schematic diagram illustrating another example of structure at a pixel of an integrated device, according to some embodiments.

FIG. 3 depicts a cut-away view of an example structure of an integrated device, according to some embodiments.

FIG. 4-1A through FIG. 4-1J depict structures associated with an example method for fabricating an optical nanostructure, according to some embodiments.

FIG. 4-2A through FIG. 4-2J depict structures associated with an example method for fabricating an optical nanostructure, according to some embodiments.

FIG. 5-1A is a block diagram depiction of an analytical instrument that includes a compact mode-locked laser module, according to some embodiments.

FIG. 5-1B depicts a compact mode-locked laser module incorporated into an analytical instrument, according to some embodiments.

FIG. 5-2 depicts a train of optical pulses, according to some embodiments.

FIG. 5-3 depicts an example of parallel reaction chambers that can be excited optically by a pulsed laser via one or more waveguides and further shows corresponding detectors for each chamber, according to some embodiments.

FIG. 5-4 illustrates optical excitation of a reaction chamber from a waveguide, according to some embodiments.

FIG. 5-5 depicts further details of an integrated reaction chamber, optical waveguide, and time-binning photodetector, according to some embodiments.

FIG. 5-6 depicts an example of a biological reaction that can occur within a reaction chamber, according to some embodiments.

FIG. 5-7 depicts emission probability curves for two different fluorophores having different decay characteristics.

FIG. 5-8 depicts time-binning detection of fluorescent emission, according to some embodiments.

FIG. 5-9 depicts a time-binning photodetector, according to some embodiments.

FIG. 5-10A depicts pulsed excitation and time-binned detection of fluorescent emission from a sample, according to some embodiments.

FIG. 5-10B depicts a histogram of accumulated fluorescent photon counts in various time bins after repeated pulsed excitation of a sample, according to some embodiments.

FIG. 5-11A-5-11D depict different histograms that may correspond to the four nucleotides (T, A, C, G) or nucleotide analogs, according to some embodiments.

FIG. 6-1A depicts a graph of refractive indexes and extinction coefficients versus wavelengths for a first exemplary silicon-rich nitride material for use in the design of an optical nanostructure, according to some embodiments.

FIG. 6-1B depicts a graph of refractive indexes and extinction coefficients versus wavelengths for a second exemplary silicon-rich nitride material for use in the design of an optical nanostructure, according to some embodiments.

The features and advantages of the present invention will become more apparent from the detailed description set forth below when taken in conjunction with the drawings. When describing embodiments in reference to the drawings, directional references ("above," "below," "top," "bottom," "left," "right," "horizontal," "vertical," etc.) may be used. Such references are intended merely as an aid to the reader viewing the drawings in a normal orientation. These directional references are not intended to describe a preferred or only orientation of features of an embodied device. A device may be embodied using other orientations.

DETAILED DESCRIPTION

I. Integrated Device with an Optical Nanostructure Rejecter

Embodiments of an optical nanostructure rejecter are described below mainly in connection with instruments that analyze samples. However, the inventive embodiments are not limited to only instruments that analyze samples. Optical nanostructure rejecters may be useful for other applications such as optical imaging devices, optical sensors, semiconductor lasers or light-emitting diodes, etc.

Instruments for analyzing samples continue to improve and may incorporate microfabricated devices (e.g., electronic chips, optoelectronic chips, microfluidic chips, etc.) which can help reduce the overall size of the instrument. Samples to be analyzed can include air (e.g., sensing for harmful gaseous leaks, combustion by-products, or toxic chemical components), water or other ingestible liquids, food samples, and biological samples taken from subjects (blood, urine, etc.) In some cases, it is desirable to have portable, hand-held instruments for analyzing samples, so that technicians or medical personnel can easily carry the instrument into the field where service is needed and analyze a sample quickly and accurately. In clinical settings, a desk-top size instrument may be desired for more complex sample analysis such as sequencing of human genes or complete blood count analysis.

In advanced analytic instruments, such as those described in U.S. Patent Application publication no. 2015/0141267 and in U.S. Pat. No. 9,617,594, both of which are incorporated herein by reference, a disposable integrated device (also referred to as "chip" and "disposable chip") may be used to perform massively parallel sample analyses. The integrated device may comprise a packaged bio-optoelectronic chip on which there can be a large number of pixels having reaction chambers arranged for parallel analyses of one sample or of different samples. For example, the number of pixels having reaction chambers on a bio-optoelectronic chip can be between about 10,000 and about 10,000,000. In some embodiments, the disposable chip may mount into a receptacle of an advanced analytic instrument and interface with optical and electronic components in the instrument. The disposable chip can be replaced easily by a user for each new sample analysis.

Figure 1:
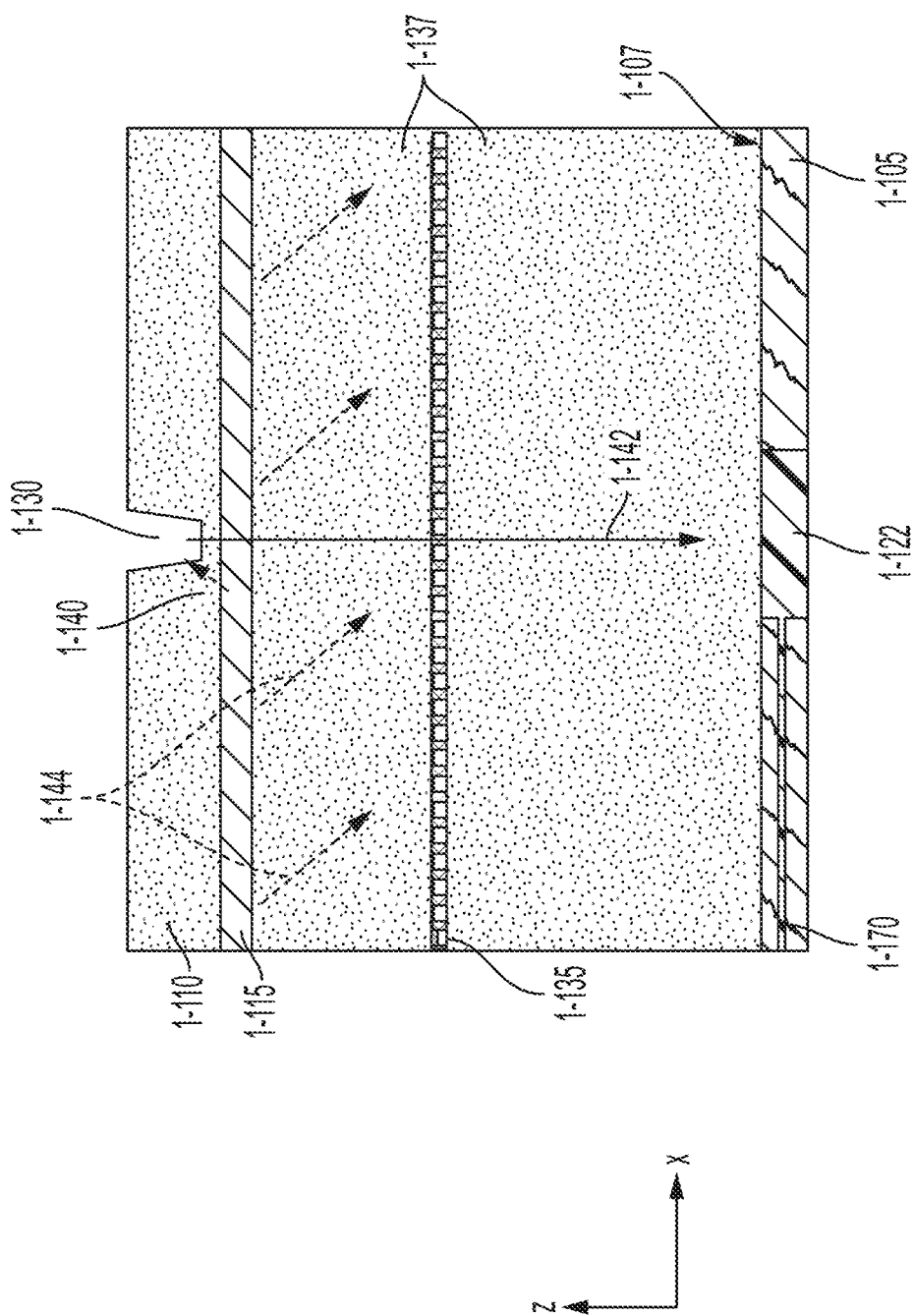
FIG. 1-1 is a schematic diagram illustrating an example of a structure at a pixel of an integrated device, according to some embodiments.

FIG. 1-1 is a simplified drawing that depicts some components that may be included in a pixel of, for example, a bio-optoelectronic chip. In a sample analysis device, a pixel can include a reaction chamber 1-130, an optical waveguide 1-115, an optical nanostructure 1-135, and a sensor 1-122 formed on a substrate 1-105. The waveguide 1-115 can transport optical energy to the pixel from a remote optical source and provide excitation radiation to the reaction chamber 1-130. Excitation radiation transported by waveguide 1-115 may be coupled to reaction chamber 1-130 via evanescent coupling in some embodiments. Arrow 1-140 depicts coupling of excitation radiation from waveguide 1-115 to reaction chamber 1-130. The excitation radiation may excite one or more analytes present in the reaction chamber 1-130. Emitted radiation from the analyte(s) can be detected by sensor 1-122. Arrow 1-142 depicts emission radiation propagating in the downward direction (although emission rays may be emitted at other angles). According to some embodiments, a signal, or lack thereof, from the sensor 1-122 can provide information about the presence or absence of an analyte in the reaction chamber 1-130. In some implementations, a signal from the sensor 1-122 can identify the type of analyte present in the reaction chamber.

For sample analysis, a sample containing one or more analytes may be deposited over the reaction chamber 1-130. For example, a sample may be disposed in a reservoir or microfluidic channel over the reaction chamber 1-130, such that the sample comes into contact with the reaction chamber. In some cases, a sample may be printed as a droplet onto a treated surface that includes the reaction chamber 1-130. During sample analysis, at least one analyte from a sample to be analyzed may enter into the reaction chamber 1-130. In some implementations, the analyte itself may fluoresce when excited by excitation radiation 1-140 delivered from the waveguide 1-115. In some cases, the analyte may carry with it one or more linked fluorescent molecules. In yet other cases, the analyte may quench a fluorophore already present in the reaction chamber 1-130. When the fluorescing entity enters into the reaction chamber and is excited by excitation radiation, the fluorescing entity can emit radiation, at a different wavelength than the excitation radiation that is detected by the sensor 1-122.

The inventors have recognized and appreciated that a portion of the excitation radiation traveling along waveguide 1-115 may radiate away from waveguide 1-115, and in some circumstances, may be received and detected by a sensor 1-122 (whether directly from the waveguide or upon reflection and/or scatter). Detection of excitation radiation may interfere with detection of emission radiation and decrease the signal-to-noise ratio. This in turn can negatively affect the device's ability to analyze or identify samples.

Radiation of excitation energy (indicated by arrows 1-144) away from waveguide 1-115 may arise due to scattering from the waveguide itself, which may result from the roughness of the waveguide's sidewalls or from the presence of other defects in the waveguide, waveguide interface with adjacent material, or in the adjacent material. Additionally, or alternatively, excitation energy may radiate away from the waveguide due to the fact that the difference between the refractive index of the waveguide's core and the refractive index of the waveguide's cladding is finite, giving rise to evanescent fields extending towards sensor 1-122.

The inventors have recognized and appreciated that detection of excitation radiation may be reduced, thus improving signal-to-noise ratio, by interposing an optical rejecter such as optical nanostructure 1-135 between waveguide 1-115 and sensor 1-122. The optical nanostructure may be configured to discriminate between signal and noise based on a difference in characteristic wavelength between the excitation radiation and the emission radiation. The optical nanostructure may be designed to reject (e.g., block or attenuate a majority of) the excitation radiation 1-144 while allowing emission radiation 1-142 to pass through and reach sensor 1-122. In some cases, a majority of emission radiation 1-142 incident on the optical nanostructure 1-135 and travelling toward the sensor 1-122 is transmitted through the optical nanostructure. In some embodiments, the optical nanostructure may include an optical nanostructure designed to exhibit at least one photonic bandgap, whereby optical energy incident on the optical nanostructure 1-135 and having a wavelength within a photonic bandgap is rejected.

The inventors have recognized and appreciated that photonic bandgap optical rejecters may be achieved by forming a periodic (or quasi-periodic) optical nanostructure, with periodicity in one, two, or three dimensions and structural variations in at least two dimensions. In some embodiments, the periodicity (or quasi-periodicity) may give rise to a spectral band in which propagation of light is prohibited (a photonic bandgap). The property is akin to Bloch waves having a certain wavelength that are prohibited inside a periodic solid-state crystal. Within the prohibited bandgap, radiation incident on the optical nanostructure interferes destructively, and as a result, is rejected. In some embodiments, an optical nanostructure may be designed so that the wavelength of the excitation radiation falls within the prohibited photonic bandgap, while the wavelength of the emission radiation falls outside the prohibited photonic bandgap. As a result, the emission radiation is transmitted and the excitations radiation is reflected. In some implementations, a majority of the emission radiation is transmitted and a majority of the excitation radiation is reflected. In some implementations, between 75% and 95% of the emission radiation is transmitted and between 75% and 95% of the excitation radiation is reflected. In some implementations, between 85% and 99% of the emission radiation is transmitted and between 85% and 99% of the excitation radiation is reflected.

According to some embodiments, an opposite performance may be obtained, whereby an optical nanostructure is designed to exhibit an allowed photonic band (rather than a prohibited photonic bandgap). In these embodiments, wavelengths within the allowed photonic band are transmitted, while wavelengths outside the allowed band are rejected. In some such embodiments, an optical nanostructure may be designed so that the wavelength of the excitation radiation falls outside the allowed photonic band, while the wavelength of the emission radiation falls within the allowed photonic band. As a result, the emission radiation is transmitted (at least in part) and the excitations radiation is reflected (at least in part) according to the amounts described above in connection with the photonic bandgap optical nanostructure.

As noted above, optical nanostructures of the types described herein are not limited to use only in connection with integrated devices having the structure described in FIG. 1-1. More generally, embodiments of optical nanostructures described herein may be used in applications in which it is desired to reject one or more wavelengths or one or more ranges of wavelengths, and it is desired to permit transmission of one or more wavelengths or one or more ranges of wavelengths. Among other possible contexts, optical nanostructures described herein may be used in conjunction with optical communication systems, optical imaging systems, Lidar systems, etc.

Figures 1, 2:
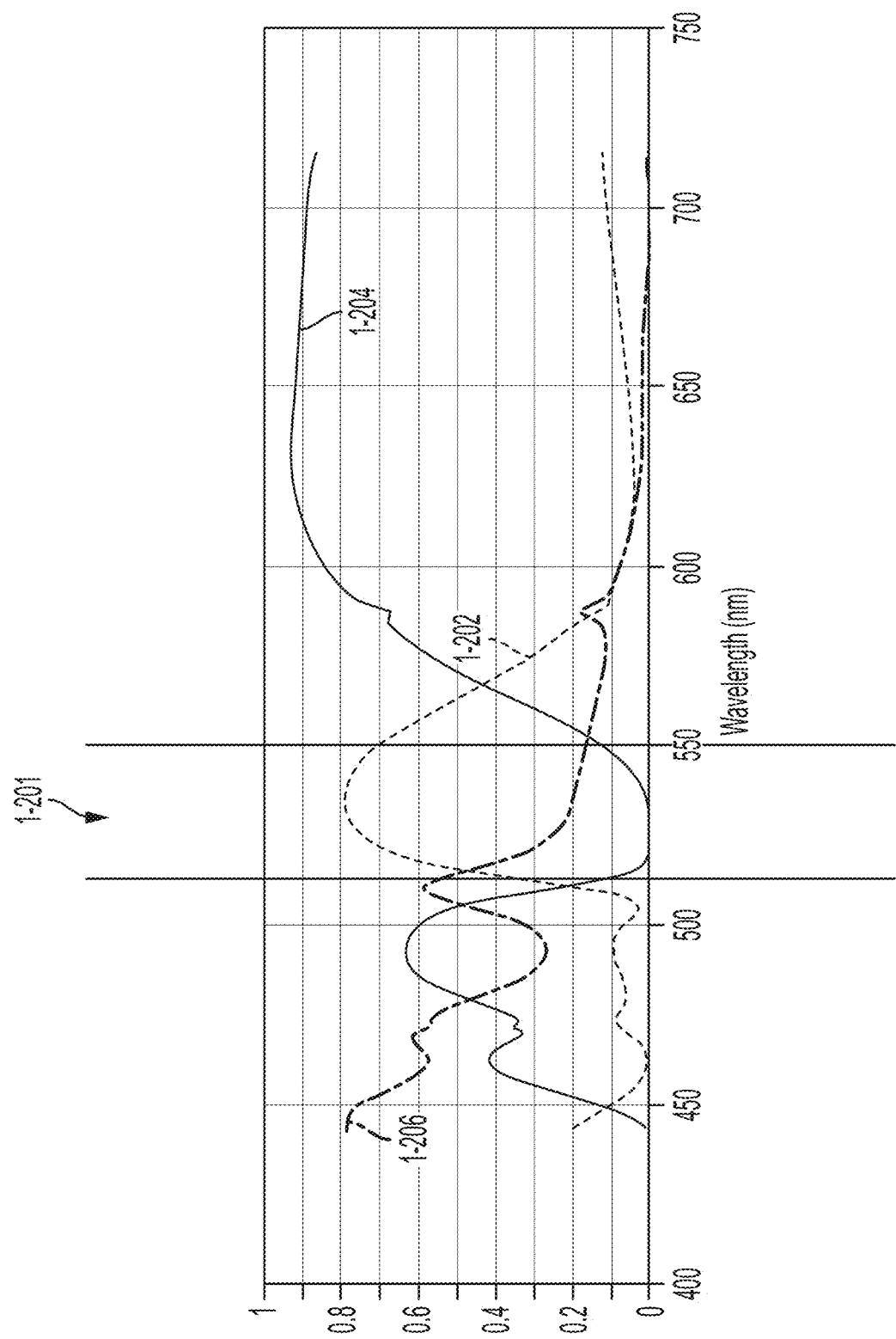

FIG. 1-2 is a plot illustrating simulated spectral responses of an example optical nanostructure, according to some embodiments. In particular, FIG. 1-2 depicts the reflection coefficient (1-202), the transmission coefficient (1-204) and the absorption coefficient (1-206) associated with the example optical nanostructure as a function of wavelength. The reflection coefficient represents the ratio between the power of the reflected radiation and the power of the incident radiation. The transmission coefficient represents the ratio between the power of the transmitted radiation and the power of the incident radiation. The absorption coefficient represents the ratio between the absorbed power and the power of the incident radiation. As illustrated in FIG. 1-2, this optical nanostructure exhibits a prohibited photonic bandgap (1-201) between approximately 515 nm and approximately 550 nm. For wavelengths within the prohibited photonic bandgap 1-201, transmission coefficient 1-204 is less than 0.1, indicating that less than 10% of the incident power passes through the optical nanostructure. The remaining power is either reflected or absorbed. In this case, 50% to 80% of the incident power is reflected, and the rest of the power is absorbed. Details of an example optical nanostructure are provided below.

For wavelengths outside the prohibited photonic bandgap 1-201, larger amounts of incident power can be transmitted through the optical nanostructure. At wavelengths greater than 570 nm, for example, 50% or more of the incident power can be transmitted. At wavelengths greater than 600 nm, 90% of more of the incident power can be transmitted. In some embodiments, an optical nanostructure may be designed so that the wavelength of the excitation radiation falls within photonic bandgap 1-201 and the wavelength of the emission radiation falls outside photonic bandgap 1-201. In one specific example for this nanostructure, the excitation radiation may have a wavelength between 510 nm and 550 nm and the emission wavelength can be between 560 nm and 700 nm. Other values of excitation and emission wavelengths are also possible for optical nanostructures designed to have a photonic bandgap at a different range of wavelengths. Photonic bandgaps may have finite bandwidths. The bandwidth may be, for example, less than 150 nm, less than 100 nm, less than 50 nm, or less than 30 nm.

For the results plotted in FIG. 1-2, the example nanostructure was a two-dimensional periodic optical nanostructure (an example of which is depicted in FIG. 1-3D). The nanostructure was arranged as a cubic structure of silicon nitride posts formed in a single layer of silicon oxide material. The periodicity p3 of the posts was 250 nm and the post width w3 was 140 nm. A thickness of the layer was 125 nm.

The spectral location of the photonic bandgap 1-201, and the values of the coefficients within and outside the photonic bandgap, may depend on different structural features of the nanostructure (e.g., periodicity, materials, post width or line width, post shape, etc.), as will be described further below. In some embodiments, the features of an optical nanostructure may be adjusted depending on the type of samples to be analyzed and/or the type of excitation source and emitters available. In some embodiments, the structural features may be adjusted so that between 25% and 15% inclusive of end values in some embodiments, between 15% and 10% inclusive of end values in some embodiments, between 10% and 5% inclusive of end values in some embodiments, and yet between 5% and 1% inclusive of end values in some embodiments, of the incident radiation within the photonic bandgap is transmitted through the nanostructure. In some cases, less than 1% of incident radiation within the photonic bandgap is transmitted through the nanostructure. In some embodiments, structural features may be adjusted so that between 50% and 75% inclusive of end values in some embodiments, between 75% and 90% inclusive of end values in some embodiments, between 90% and 95% inclusive of end values in some embodiments, and yet between 95% and 99% inclusive of end values in some embodiments, of incident radiation outside the photonic bandgap is transmitted through the optical nanostructure. In some cases, more than 99% of the incident radiation outside the photonic bandgap is transmitted through the optical nanostructure.

The spectral response of FIG. 1-2 relates to an optical nanostructure designed to exhibit a prohibited photonic bandgap, whereby radiation with wavelengths within the photonic bandgap is rejected and radiation with wavelengths outside the photonic bandgap is transmitted. Alternatively, optical nanostructures may be designed to exhibit an allowed photonic band, whereby radiation with wavelengths within the allowed photonic band is transmitted and radiation with wavelengths outside the allowed photonic band is rejected. The spectral response of one such nanostructure (not illustrated in FIG. 1-2) may exhibit a high transmission coefficient (e.g., between 50% and 75% inclusive of end values in some embodiments, between 75% and 90% inclusive of end values in some embodiments, between 90% and 95% inclusive of end values in some embodiments, and yet between 95% and 99% inclusive of end values in some embodiments) within the allowed photonic band, and a low transmission coefficient (e.g., between 25% and 15% inclusive of end values in some embodiments, between 15% and 10% inclusive of end values in some embodiments, between 10% and 5% inclusive of end values in some embodiments, and yet between 5% and 1% inclusive of end values in some embodiments) outside the allowed photonic band. Such an optical nanostructures may be designed so that the wavelength of the excitation radiation falls outside the allowed photonic band and the wavelength of the emission radiation falls within the allowed photonic band.

Referring back to FIG. 1-1, reaction chamber 1-130 may be formed into a transparent or semitransparent layer 1-110. The reaction chamber may have a depth between 50 nm and 1 µm, according to some embodiments. A minimum diameter of the reaction chamber 1-130 may be between 50 nm and 300 nm in some embodiments. If the reaction chamber 1-130 is formed as a zero-mode waveguide, then the minimum diameter may be even less than 50 nm in some cases. If large analytes are to be analyzed, the minimum diameter may be larger than 300 nm. The reaction chamber may be located above the optical waveguide 1-115 such that a bottom of the reaction chamber may be up to 500 nm above a top of the waveguide 1-115. The transparent or semitransparent layer 1-110 can be formed from an oxide or a nitride, according to some embodiments, so that excitation radiation from the optical waveguide 1-115 and emission radiation from the reaction chamber 1-130 will pass through the transparent or semitransparent layer 1-110 without being attenuated by more than 10%, for example.

In some implementations, there can be one or more additional transparent or semitransparent layers 1-137 formed on the substrate 1-105 and located between the substrate and the optical waveguide 1-115. These additional layers may be formed from an oxide or a nitride, and may be of the same type of material as the transparent or semitransparent layer 1-110, in some implementations. The optical nanostructure 1-135 may be formed within these additional layers 1-137 between the waveguide 1-115 and sensor 1-122, for example. A distance from the bottom of the optical waveguide 1-115 to the sensor 1-122 can be between 500 nm and 10 µm.

In various embodiments, the substrate 1-105 may comprise a semiconductor substrate, such as silicon. However, other semiconductor materials may be used in some embodiments. The sensor 1-122 may comprise a semiconductor photodiode that is patterned and formed on the substrate 1-105. The sensor 1-122 may connect to other complementary metal-oxide-semiconductor (CMOS) circuitry on the substrate via interconnects 1-170.

An optical nanostructure 1-135 may be arranged to exhibit a prohibited photonic bandgap or an allowed photonic band. As described above, the spectral location of the photonic bandgap or allowed band may be chosen to reject excitation radiation and allow emission radiation to pass through the nanostructure to the sensor 1-122. In some embodiments, an optical nanostructure 1-135 is patterned to include structural variations and periodicity in a plane parallel to a surface (e.g., surface 1-107) of the substrate (the xy-plane in FIG. 1-1). In some embodiments, optical nanostructure 1-135 may have structural variations that are periodic (or quasi-periodic) in the xy-plane. The structural variations may be periodic (or quasi-periodic) in one dimension, such as along the x-axis or the y-axis, or in two dimensions, such as along the x-axis and the y-axis. In some embodiments, the structural variations may involve two or more materials of different refractive indexes.

An example of an optical nanostructure having periodicity in one dimension and structural variations in at least two dimensions is depicted in FIGS. 1-3A, in accordance with some embodiments. In an implemented one-dimensional structure, the bars may extend a finite distance in the y direction that is much greater than the periodicity or pitch P1. In some implementations, the extended distance in the y direction is much larger than a region of interest (e.g., diameter of reaction chamber 1-130, width of waveguide 1-115, or diameter of sensor 1-122). FIG. 1-3A illustrates an optical nanostructure that is periodic along one axis (the x-axis in this example) that is parallel or substantially parallel to surface 1-107 of substrate 1-105. In this example, optical nanostructure 1-135 includes two materials (1-302 and 1-304) alternating along the x-axis in a periodic fashion. Materials 1-302 and 1-304 have different refractive indexes at the wavelength of the emission radiation and/or have different refractive indexes at the wavelength of the excitation radiation. In some embodiments, an optical nanostructure has no missing or significantly different periodic component within the structural variations. It should be appreciated that, in some embodiments, more than two materials may be used and may be arranged in a periodic pattern (e.g., alternating of two materials or adding a third material periodically into the illustrated pattern).

Any suitable materials 1-302 and 1-304 may be used to form an optical nanostructure according to embodiments described herein. Example materials include, but are not limited to, one or both of dielectric and conductive materials. Examples of such dielectric and conductive materials include silicon (amorphous, nano-crystalline, micro-crystalline, mono-crystalline or poly-crystalline, doped or undoped), silicon nitride, silicon carbide, silicon oxide and alloys or mixtures thereof (including silicon-rich nitride and/or nitrogen-doped silicon, among others), air, polymer, aluminum, copper, titanium nitride, tungsten, titanium oxide, germanium, tantalum, etc. In one example, material 1-302 includes silicon and material 1-304 includes silicon nitride. In another example, material 1-302 includes silicon and material 1-304 includes silicon oxide. In another example, material 1-302 includes silicon and material 1-304 includes a polymer. In another example, material 1-302 includes silicon nitride and material 1-304 includes silicon oxide. In another example, material 1-302 includes silicon nitride and material 1-304 includes air. Other combinations are also possible.

The inventors have discovered that certain materials may be used in the design of an optical nanostructure 1-135 to optimize performance, including silicon-rich nitride materials having specific n (refractive index) and k (extinction coefficient) values. Such materials may be used as filters in the design of an optical nanostructure, for example, or used to form an optical nanostructure 1-135 as described herein. Non-limiting examples of these materials include Silicon-rich Nitride materials. Characteristics of two examples of Silicon-rich Nitride materials—Silicon-rich Nitride I and Silicon-rich Nitride II—are respectively shown in the graphs of FIGS. 6-1A and 6-1B. Shown in each graph are the n and k values of the material versus wavelength.

In the illustrated example of FIG. 1-3A, an optical nanostructure 1-135 includes a unit cell that is repeated periodically along the x-axis. The periodicity (P1) with which the unit cell is repeated may be between 150 nm and 2 µm in some embodiments, between 150 nm and 1 µm in some embodiments, between 150 nm and 500 nm in some embodiments, between 150 nm and 400 nm in some embodiments, between 150 nm and 300 nm in some embodiments, between 200 nm and 300 nm in some embodiments, between 230 nm and 270 nm in some embodiments, or between 240 nm and 260 nm in some embodiments. Other ranges are also possible. The width (W1) of a first material 1-302 along the x-axis may be between 50 nm and 1 µm in some embodiments, between 50 nm and 500 nm in some embodiments, between 100 nm and 500 nm in some embodiments, between 100 nm and 300 nm in some embodiments, between 150 nm and 300 nm in some embodiments, between 100 nm and 250 nm in some embodiments, between 150 nm and 250 nm in some embodiments, between 100 nm and 150 nm in some embodiments, between 150 nm and 200 nm in some embodiments, between 130 nm and 150 nm in some embodiments, or between 130 nm and 140 nm in some embodiments. In some embodiments, periodicity P1 and width W1 may be selected so that the spectral response of the resulting optical nanostructure rejects excitation radiation and allows emission radiation to pass through. For example, P1 and W1 may be selected so that the characteristic wavelength of a selected excitation radiation falls within a prohibited photonic bandgap and the characteristic wavelength of a resulting emission radiation falls outside the prohibited photonic bandgap, or so that the wavelength of the emission radiation falls within an allowed photonic band and the wavelength of the excitation radiation falls outside the allowed photonic band.

Materials 1-302 and 1-304 may be formed into an optical nanostructure in any suitable way, such as using a fabrication process discussed below in connection with FIGS. 4-1A through 4-1J. In some embodiments, materials 1-302 and 1-304 may be patterned through one or more lithographic steps, e.g., by using appropriately designed photomask(s) and photolithography processes. In some embodiments, material 1-302 includes a plurality of bars extending along the y-axis, as shown in the example of FIG. 1-3A, though different shapes and orientations are also possible.

In some embodiments, an optical nanostructure 1-135 may include multiple material layers arranged in a periodic or quasi-periodic fashion. Having multiple layers, in some embodiments, may improve the transmission and/or the reflection coefficient of the optical nanostructure. For example, having multiple layers may result in an increase in the reflection coefficient within a prohibited photonic bandgap and an increase in the transmission coefficient outside the prohibited photonic bandgap, or may result in an increase in the transmission coefficient within an allowed photonic band and an increase in the reflection coefficient outside the allowed photonic band.

FIG. 1-3B illustrates an example elevation view of a nanostructure having multiple material layers arranged in a periodic fashion, in accordance with some embodiments. This example illustrates an optical nanostructure having four layers that are stacked in the z direction, but any other suitable number of layers may be used. In a multilayer optical nanostructure, each layer may be formed at a different location along an axis perpendicular to surface 1-107 of a substrate 1-105 (e.g., along the z-axis). Each layer may include patterned materials 1-302, 1-304 that is periodic in one dimension (as shown for example in FIG. 1-3A), or periodic in two dimensions (e.g., along the x-axis and the y-axis) in some cases. The optical nanostructure of FIG. 1-3B includes a first plurality of discrete regions (1-302) of first material (e.g., dielectric material or conductive material), and a second plurality of discrete regions (1-304) of second material having a different index of refraction (dielectric material, conductive material, or air).

In some embodiments, the discrete regions of one layer are staggered with respect to the discrete regions of another layer. In the example optical nanostructure of FIG. 1-3B, for example, each of the first and third layers is staggered along the x-axis with respect to the second and fourth layers.

Each layer of a multilayer optical nanostructure may have a height (H1) or thickness that is between 50 nm and 1 µm in some embodiments, between 50 nm and 500 nm in some embodiments, between 100 nm and 500 nm in some embodiments, between 100 nm and 300 nm in some embodiments, between 150 nm and 300 nm in some embodiments, between 100 nm and 250 nm in some embodiments, between 150 nm and 250 nm in some embodiments, between 100 nm and 150 nm in some embodiments, between 150 nm and 200 nm in some embodiments, between 120 nm and 150 nm in some embodiments, between 120 nm and 140 nm in some embodiments, between 120 nm and 130 nm in some embodiments, or between 130 nm and 140 nm in some embodiments. Other ranges are also possible. Different layers may have different heights. Alternatively, all the layers may have essentially the same height.

In some embodiments, an optical nanostructure may have structural variations that are periodic or quasi-periodic in two dimensions within a plane. Examples of optical nanostructures having structural variations in two dimensions within a plane are depicted in FIGS. 1-3C and 1-3D. In the example of FIG. 1-3C, columns of a second material 1-314 are separated from each other by regions of a first material 1-312. The first and second materials 1-312, 1-314 may be any of the materials described above for materials 1-302, 1-304. In the example of FIG. 1-3C, the second material 1-314 may have a lower value of index of refraction than the first material 1-312. In the example of FIG. 1-3D, columns of a first material 1-322 are separated from each other by regions of a second material 1-324. The first and second materials 1-322, 1-324 may be any of the materials described above for materials 1-302, 1-304. In the example of FIG. 1-3D, the second material 1-324 may have a higher value of index of refraction than the first material 1-322.

Figures 1, 2, 3, 3D:
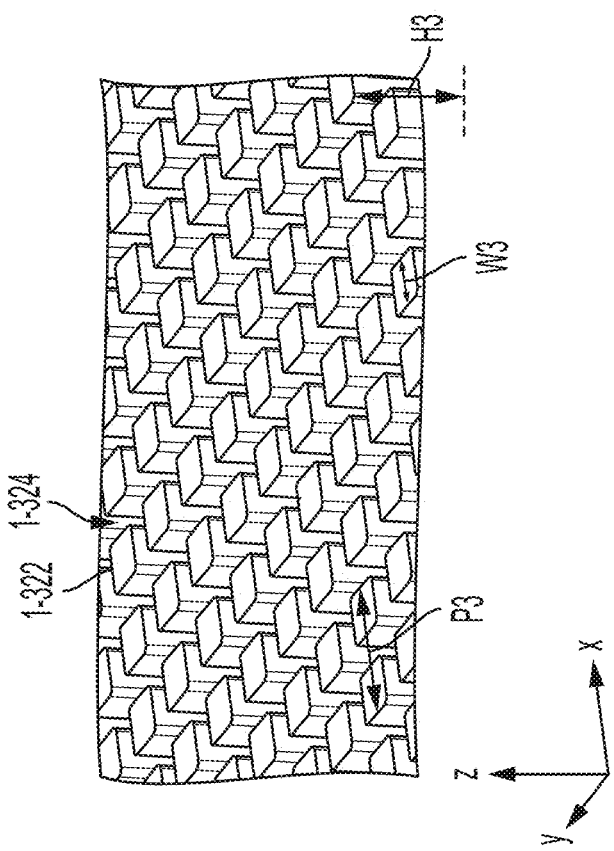
Figures 1, 2, 3, 3C:
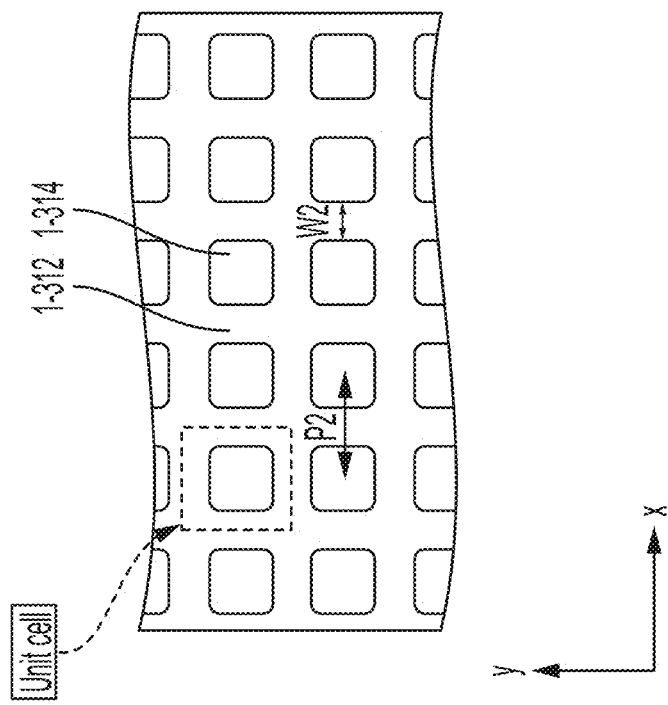
Figures 1, 2, 3, 3F:
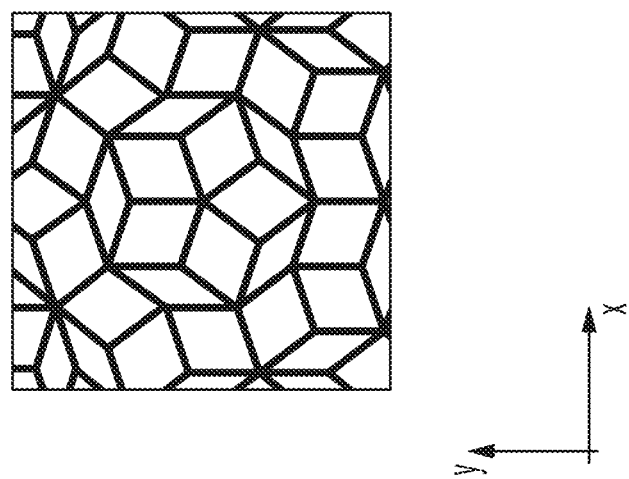
Figures 1, 2, 3, 3E:
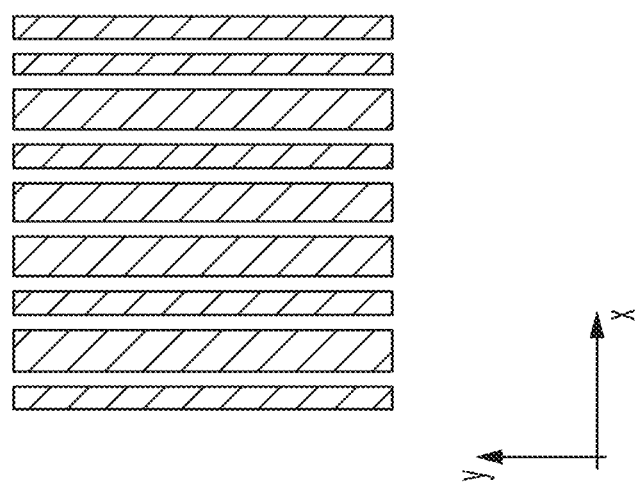

For the examples depicted in FIG. 1-3C and FIG. 1-3D, the periodicities along the x-axis (P2 and P3) may have a value in any of the ranges described above in connection with FIG. 1-3A. Similarly, the periodicities along the y-axis may have a value in any of the ranges described above in connection with FIG. 1-3A. A feature formed from one material within a unit cell of a planar, two-dimensional optical nanostructure may have any suitable shape, such as square, rectangular, polygonal, triangular, circular, or irregular. Widths (W2 and W3) of structural features along the x-axis may have a value in any of the ranges described above in connection with FIG. 1-3A. Similarly, widths of structural features along the y-axis may have a value in any of the ranges described above in connection with FIG. 1-3A. In some embodiments, multiple layers of a planar, two-dimensional optical nanostructure, such as those shown in FIG. 1-3C or FIG. 1-3D, may be formed in a stack along the z-axis. The layers may be staggered similar to the arrangement of FIG. 1-3B. The height (H3) of each layer may have a value in any of the ranges described above in connection with FIG. 1-3B.

Compared to optical nanostructures periodic in one dimension, those periodic in two or three dimensions provide additional design parameters. As a result, optical nanostructures periodic in two or three dimensions provide greater flexibility to engineer a desired spectral response. In some embodiments, for example, optical nano structures periodic in two or three dimensions have flatter spectral responses within the photonic bandgap or allowed photonic band and/or steeper roll-offs at edges of the photonic bandgap or allowed photonic band. Steeper roll-offs can lead to a greater differential between the transmission coefficient and the reflection coefficient excitation and emission wavelengths that are near an edge of the photonic bandgap or allowed band.

The examples described in connection with FIGS. 1-3A, 1-3B, 1-3C and 1-3D exhibit periodicities in one or two dimensions. Additionally, or alternatively, quasi-periodic optical nanostructures may be used to achieve a spectral response characterized by prohibited photonic bandgap or allowed photonic band. Quasi-periodic optical nanostructures of the types described therein may include two or more alternating building blocks, in accordance with some embodiments. Examples of quasi-periodic optical nanostructures include one dimensional photonic structures based on the Fibonacci sequence (shown in FIG. 1-3E), two dimensional photonic structures based on the Penrose structure (shown in FIG. 1-3F), three dimensional photonic structures with icosahedral quasi-crystalline structures, one, two or three dimensional photonic structures based on the Thue-Morse sequence, one, two or three dimensional photonic structures based on the period-doubling sequence, one, two or three dimensional photonic structures based on the Rudin-Shapiro sequence, one, two or three dimensional photonic structures based on the Cantor sequence, and others. Some such structures may give rise to spectral responses with photonic bandgaps or allowed bands even if they do not have translational symmetry. Quasi-periodic structures of the types described herein may be deterministically aperiodic.

Referring back to FIG. 1-1, the presence of an optical nanostructure between waveguide 1-115 and sensor 1-122 may result in the rejection of excitation radiation 1-144 while allowing transmission of emission energy 1-142. The excitation radiation 1-144 may come directly from waveguide 1-115 and/or be scattered from other surfaces of the device. The inventors have recognized and appreciated that an optical nanostructure of the present embodiments can be more effective at reducing transmission of excitation radiation 1-144 from a wide range of angles than, for example, a multilayer dielectric interference filter.

FIGS. 1-4A and 1-4B depict example electric field patterns calculated for an integrated device having example structure similar to that depicted in FIG. 1-1. However, a microdisk is included in the simulation and is located between the waveguide 1-115 and the optical nanostructure 1-135. The microdisk is described further below and helps concentrate emission radiation onto the sensor 1-122. For this simulation, the waveguide 1-115 and optical nanostructure comprise silicon nitride surrounded by silicon oxide. The optical nanostructure is formed as a single-layer, planar, two-dimensional nanostructure having a cubic crystal like that shown in FIG. 1-3D. The first material 1-322 is formed from silicon nitride and the second material 1-324 is formed from silicon oxide. The pitch P3 is 260 nm, the width W3 is 160 nm, and the thickness of the layer H3 is 125 nm for this example.

For this example simulation the excitation radiation has a characteristic wavelength ($\lambda=\lambda_{excitation}$) of 532 nm and at the emission radiation has a characteristic wavelength ($\lambda=\lambda_{emission}$) of 572 nm. Other optical nanostructure parameters (periodicity, width, thickness, etc.) and/or other wavelengths (including for example excitation wavelengths in the 500 nm-540 nm range to produce emission wavelengths in the 620 nm-650 nm range) may be used in other embodiments. The electric fields patterns were computed with software that solves Maxwell's equations (e.g., using a finite-difference time-domain analysis) within the simulation domain with the following initial conditions for the excitation and emission radiation: 1) radiation at $\lambda=\lambda_{excitation}$ is coupled into the single-mode waveguide 1-115 from an external source, and 2) radiation at $\lambda=\lambda_{emission}$ is generated in the reaction chamber 1-130.

As illustrated in FIG. 1-4A for $\lambda=\lambda_{excitation}$, a significant portion of the electric field is confined within waveguide 1-115 which delivers the excitation radiation to the reaction chamber 1-130. However, an appreciable amount of the electric field for the excitation radiation extends below the waveguide 1-115 due to an evanescent field associated with the waveguide and scatter from walls of the waveguide and other structure within the pixel that includes the reaction chamber. The optical nanostructure 1-135 can reflect most of the excitation electric field back toward the waveguide. Absent optical nanostructure 1-135, the electric field may reach sensor 1-122 and contribute to background noise. This result would be undesirable as it may reduce the signal-to-noise ratio of the detection system. Use of an optical nanostructure between waveguide 1-115 and sensor 1-122 leads to a substantial reduction in the magnitude of the electric field in the region adjacent to sensor 1-122. As a result, the amount of detected excitation energy is reduced significantly.

As illustrated in FIG. 1-4B, emission radiation at $\lambda=\lambda_{emission}$ proceeding from the reaction chamber 1-130 toward the sensor is mostly transmitted through the optical nanostructure 1-135 and can travel to the sensor 1-122. As noted above, the microdisk 145 helps concentrate or condense emission radiation onto the sensor 1-122.

The inventors have further recognized that excitation radiation may strike optical nanostructure 1-135 at different incident angles in some circumstances. This may be due, among other possible reasons, as a result of the excitation radiation being reflected multiple times and scattering off structure within the pixel before striking the optical nanostructure. Recognizing this problem, the inventors have appreciated that an advantageous characteristic of an optical nanostructure of the present embodiments is a capability to reject radiation over a wider range of incident angles than multilayer interference filters, for example.

Compared to other types of optical rejecters, the optical nanostructures of the types described herein provide optical rejection across wide ranges of incident angles. For a single layer optical nanostructure, this behavior is due to the presence of periodic or quasi-periodic structural variations (in one or two dimensions) in the xy-plane. FIG. 1-5 is a plot illustrating a rejection ratio associated with two different optical structures at wavelengths of interest plotted as a function of angle of incidence (horizontal axis). The rejection ratio is a ratio of an amount of emission radiation at a characteristic emission wavelength (572 nm in this example) transmitted through the optical structure divided by an amount of excitation radiation at a characteristic excitation wavelength (532 nm in this example) that is transmitted through the optical structure. A same amount of power is incident on the optical structure for the emission radiation and excitation radiation. The angle of incidence is measured with respect to a normal to the planar surface of the optical structure.

A first rejection ratio curve 1-501 is plotted for a multilayer interference filter having 23 layers (though any other number of layers may be used, such as between 10 and 50 layers, between 10 and 40 layers, between 20 and 50 layers, or between 20 and 40 layers, among others) with alternating refractive indexes along the z-axis. This optical structure does not exhibit structural variations in the xy-plane. Thus, in each xy-plane, the refractive index is uniform. The rejection ratio for this optical structure is relatively high below 20°, but drops significantly for incident angles greater than 20°. This drop means that an appreciable amount of excitation radiation striking the optical structure with angles greater than about 22° is transmitted through the optical structure and can contribute to background signal at the sensor 1-122.

A second rejection ratio curve 1-502 is plotted for an example single-layer optical nanostructure of the present embodiments having in-plane structural variations. The example optical nanostructure has a cubic lattice with essentially square columns of silicon nitride embedded in silicon oxide. The columns have a width of 140 nm and the periodicity in both the x and y directions is 250 nm. A thickness of the layer is 125 nm. As illustrated in FIG. 1-5, the rejection ratio is greater than about 10 for all angles below 45°. Hence, this optical nanostructure can provide better rejection of excitation radiation over a wider range of incident angles than multilayer interference filters.

Another example of optical structures that may be included at a pixel of an integrated device is shown in FIG. 2-1. According to some implementations, one or more iris layers 2-110 may be formed above the sensor 1-122. An iris layer 2-110 may include an opening or hole 2-112 through a light-reducing material. The light-reducing material may comprise a metal, polymer, semiconductor, or any material that rejects (e.g., absorbs and/or reflects) a majority of excitation radiation incident on the iris layer 2-110. The light-reducing material may also reject emission radiation in some cases. The hole 2-112 can allow emission from the reaction chamber 1-130 to pass through the iris layer 2-110 and reach sensor 1-122, while the light-reducing material blocks or attenuates radiation from other directions (e.g., from adjacent pixels or from scattered excitation radiation). For example, an iris layer 2-110 can block or attenuate scattered excitation radiation at wide angles of incidence from striking the sensor 1-122 and contributing to background noise. In some embodiments, an iris layer 2-110 may be formed from a conductive material and provide a potential reference plane or grounding plane for circuitry formed on or above the substrate 1-105. In some embodiments, an iris layer 2-110 may be formed from a dielectric material. The hole 2-112 in the iris layer may be shaped in any suitable way, such as a square, rectangle, disk, ellipse, polygon, etc.

In the example of FIG. 2-1, two iris layers 2-110 are included. One iris layer is disposed between waveguide 1-115 and optical nanostructure 1-135. Another iris layer is disposed between optical nanostructure 1-135 and sensor 1-122. It should be appreciated, however, that any other suitable number of iris layers and locations may be used. In some cases, a single iris layer may be used and may be located between the reaction chamber 1-130 and optical nanostructure 1-135 or between the optical nanostructure 1-135 and sensor 1-122.

In some embodiments, a condensing optical element 2-160 may be used to concentrate emission radiation emitted from the reaction chamber onto the sensor. In the example of FIG. 2-1, a condensing optical element 2-160 is located between the reaction chamber 1-130 and the optical nanostructure 1-135, though other placements are also possible. According to some embodiments, a condensing optical element 2-160 may be made of one or more materials transparent at the wavelength of the emission radiation, and with a refractive index different (e.g., greater) than the refractive index of the material surrounding the condensing optical element 2-160. In this way, the condensing optical element 2-160 can provide some focusing of emission radiation from the reaction chamber 1-130. In some embodiments, an optical element 2-160 may be shaped as a disk (e.g., a microdisk), thereby providing rotational symmetry. Optical element 2-160 may be positioned such that the center of the disk is aligned, along the z-axis, with the center of the reaction chamber 1-130. In some embodiments, reaction chamber 1-130, optical element 2-160, irises 2-112 and sensor 1-122 may be aligned to one another along the z-axis.

According to some embodiments, devices of the types described herein may fabricated by successive steps of material deposition and patterning to build up the multiple levels in a chip for an integrated device. In some implementations, a chip for an integrated device may be obtained by bonding two substrates or wafers to one another. For example, an integrated device (for which example structure at a pixel is depicted in FIG. 2-1) may be formed from a bio-optical substrate 1-100 that can be aligned and bonded to a CMOS substrate 1-101. An example bio-optical substrate 1-100 can include several pixels, each pixel having a reaction chamber 1-130, a waveguide 1-115, an optical nanostructure 1-135, and optionally, one or more iris layers 2-110 and one or more optical elements 2-160. An example CMOS substrate 1-101 can include several corresponding pixels having sensors 1-122 (e.g., one per pixel) and circuitry for processing signals generated by the sensors. Layers 2-202 represent conductor layers or semiconductor layers that may be used for routing and/or processing the signals.

The effect of a pair of iris layers 2-110 and a condensing optical element 2-160 is depicted in FIG. 2-2, in accordance with some embodiments. As illustrated, rays emitted substantially parallel to the z-axis pass straight through the openings in the iris layers. Rays emitted with angles deviating substantially from the z-axis are rejected by one of the iris layers 2-110. Rays emitted with smaller angles are focused by the optical element 2-160. As a result, radiation emitted from reaction chamber 1-130 is concentrated onto sensor 1-122, thus increasing the signal-to-noise ratio.

Another example of a structure that may be included at a pixel of an integrated device is shown in FIG. 2-3. According to some implementations, one or more light-reducing layers 2-150 may be formed over layer 1-110, into which a reaction chamber 1-130 may be formed. The light-reducing layers 2-150 may be formed from one or more metal layers. In some cases, the light-reducing layers 2-150 may include a semiconductor and/or oxide layer. The light-reducing layers 2-150 may reduce or prevent excitation radiation from the optical waveguide 1-115 from travelling into a sample above the reaction chamber 1-130 and exciting fluorophores within the sample. Additionally, the light-reducing layers 2-150 can prevent external radiation from above the reaction chamber to pass through to the sensor 1-122. Emission from outside the reaction chamber can contribute to unwanted background radiation and signal noise. Light-reducing layers 2-150 may be used in conjunction with any of the embodiments described herein.

Example structure 3-100 for a disposable chip is shown in FIG. 3, according to some embodiments. The disposable chip structure 3-100 may include a bio-optoelectronic chip 3-110 having a semiconductor substrate 3-105 and including a plurality of pixels 3-140 formed on the substrate. Each pixel 3-140 may have a structure and an embodiment of an optical nanostructure as described above in connection with FIG. 1-1 through FIG. 2-3. In some embodiments, there may be rows (or columns) of waveguides 3-115 that provide excitation radiation to rows (or columns) of pixels 3-140. Waveguide 1-115 of FIG. 1-1 may serve as any one of such waveguides in some implementations. Excitation radiation may be coupled into the waveguides, for example, through an optical port 3-150. In some embodiments, a grating coupler may be formed on the surface of the bio-optoelectronic chip 3-110 to couple excitation radiation from a focused beam into one or more receiving waveguides that connect to the plurality of waveguides 3-115.

The disposable chip structure 3-100 may further include walls 3-120 that are formed around a pixel region on the chip 3-110. The walls 3-120 may be part of a plastic or ceramic casing that supports the chip. The walls 3-120 may form at least one reservoir 3-130 into which at least one sample may be placed and come into direct contact with reaction chambers 1-130 on the surface of the bio-optoelectronic chip 3-110. The walls 3-120 may prevent the sample in the reservoir 3-130 from flowing into a region containing the optical port 3-150 and grating coupler, for example. In some embodiments, the disposable chip structure 3-100 may further include electrical contacts on an exterior surface of the disposable chip and interconnects within the package, so that electrical connections can be made between circuitry on the bio-optoelectronic chip 3-110 and circuitry in an instrument into which the chip is mounted.

As noted above, an optical nanostructure 1-135 is not limited only to a disposable chip 3-100 as depicted in FIG. 3. Example embodiments of an optical nanostructure 1-135 may be included in other chips, such as imaging chips having photosensor arrays. Such imaging chips may be used in cameras, video cameras, smart phones, and optical sensing arrays.

II. Methods for Fabricating Optical Nanostructures

Figures 1, 2, 3, 4, 4B:
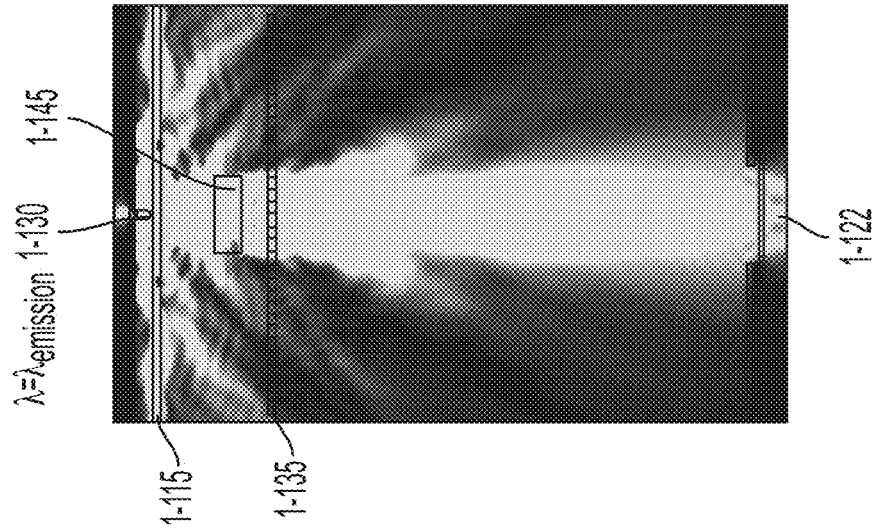
Figures 1, 2, 3, 4, 4A:
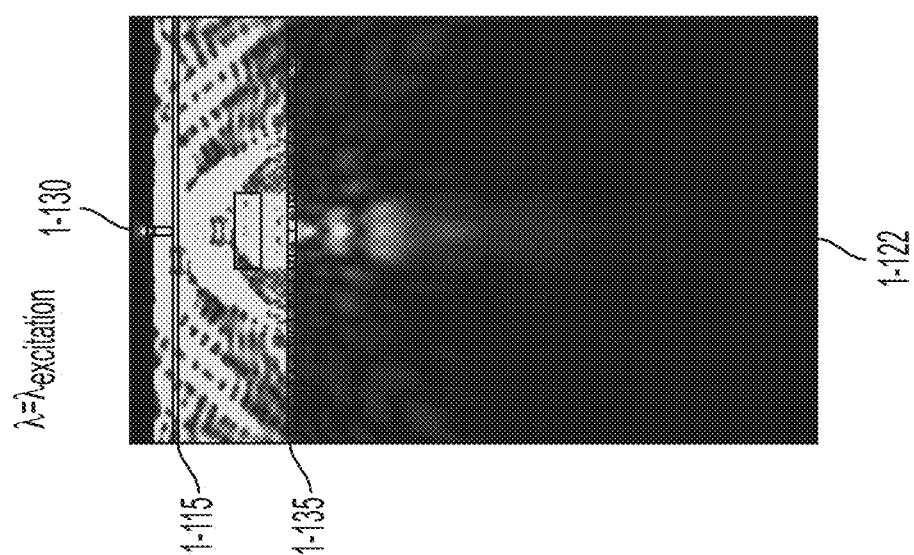
Figures 1A, 5:
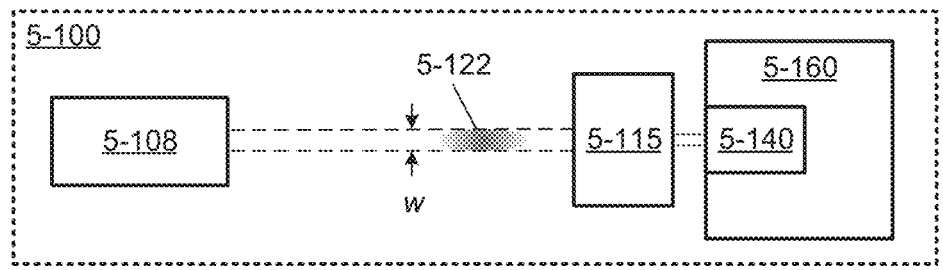

FIGS. 4-1A through 4-1J illustrate, example structure associated with a method for fabricating an optical nanostructure (such as any one of the optical nanostructures described above). In the process step depicted in FIG. 4-1A, a substrate 4-100 is provided or obtained upon which lithography steps may be performed. Substrate 4-100 may include some structure already formed on the substrate 4-100. For example, a substrate 4-100 may include part of the structure shown in FIG. 1-1 or FIG. 2-1 below the optical nanostructure 1-135. In some embodiments, substrate 4-100 may comprise a bulk semiconductor substrate, though other types of bulk substrates may be used in some implementations.

Figures 1B, 5:
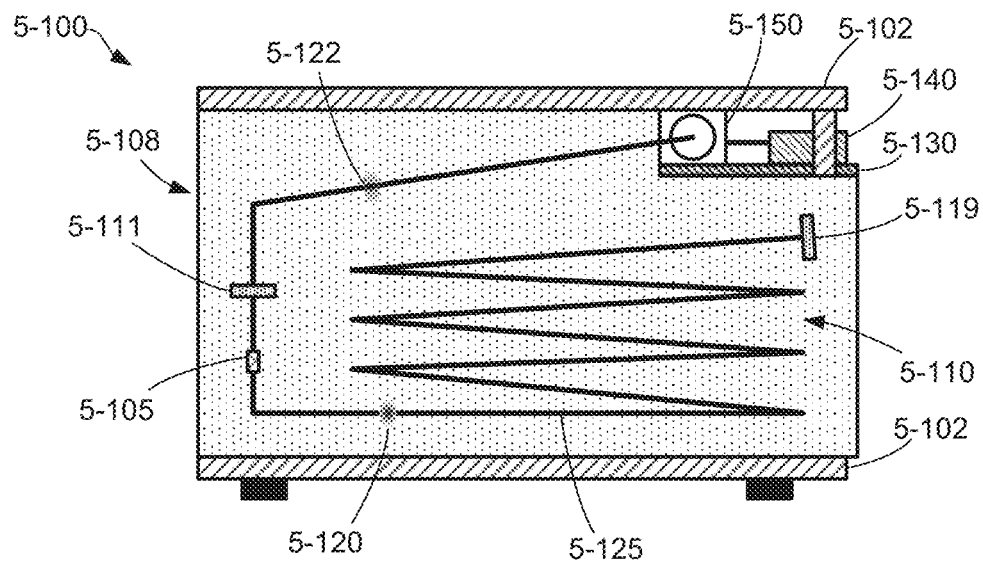
Figures 2, 5:
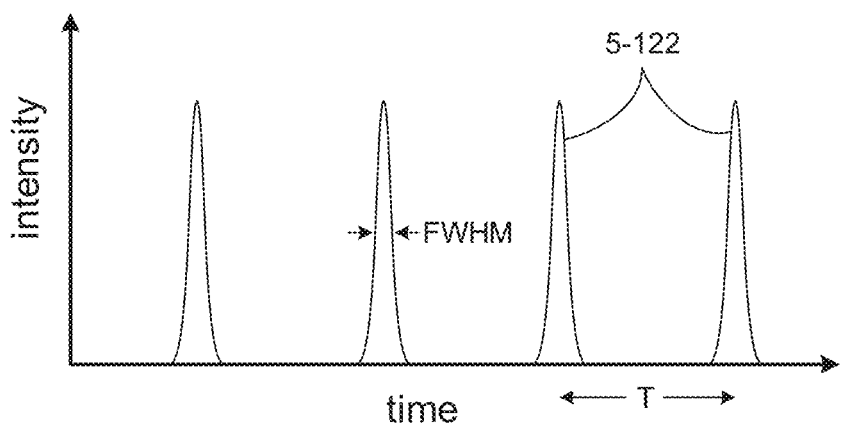
Figures 3, 5:
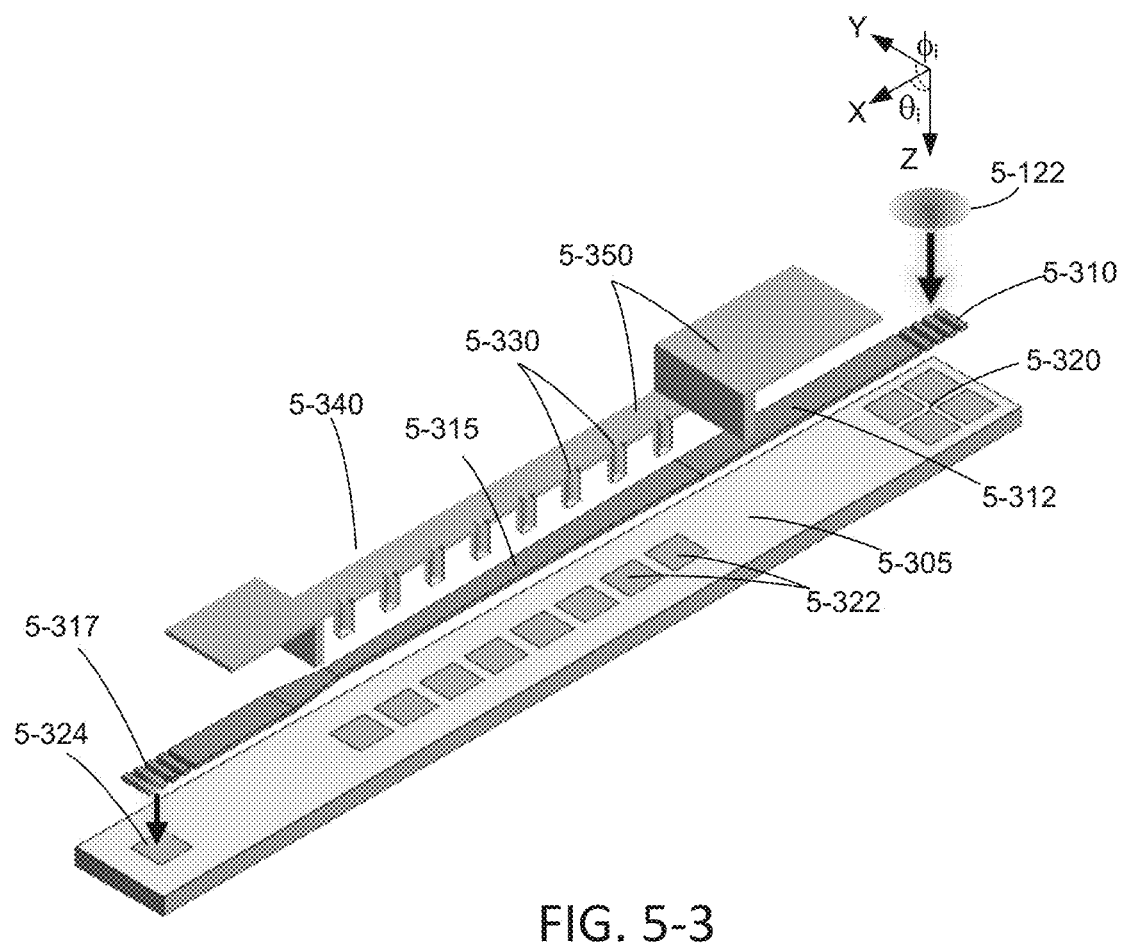
Figures 4, 5:
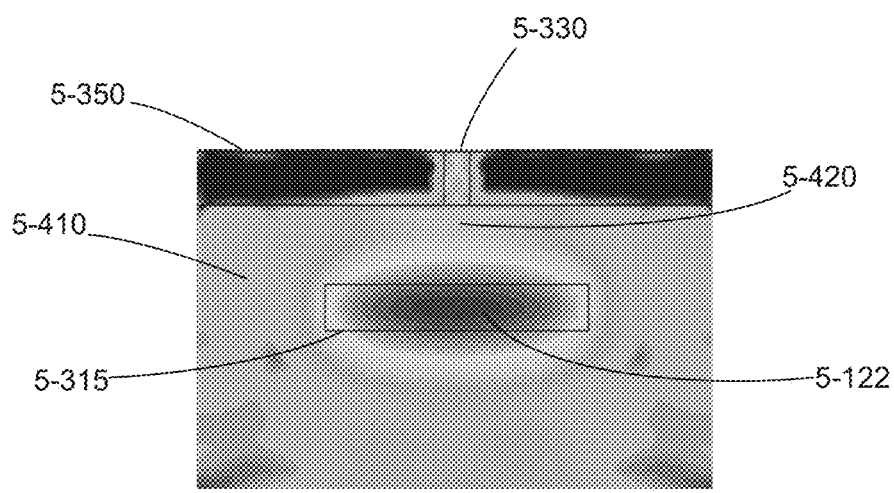
Figure 5:
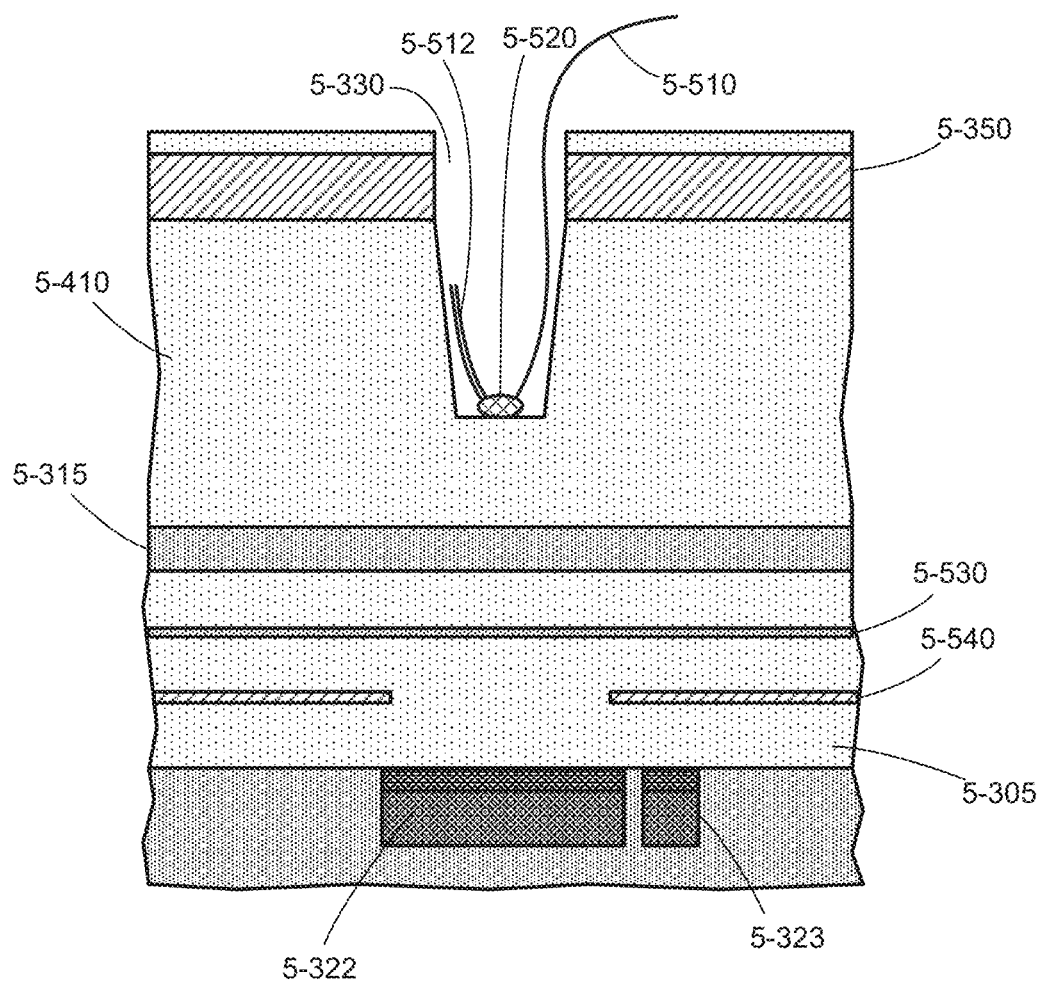

According to some embodiments, a first material layer 4-102 may be deposited or grown on substrate 4-100, as depicted in FIG. 4-1B. The first material layer 4-102 may be deposited, for example, by physical vapor deposition (PVD), plasma-enhanced chemical vapor deposition (PECVD), high-density plasma (HDP) PECVD, or sputtering. The first material layer 4-102 may include amorphous silicon, silicon nitride, titanium nitride, titanium oxide, among other possible materials described above for an optical nanostructure 1-135 silicon-rich nitride materials having specific n (refractive index) and k (extinction coefficient) values such as Silicon-rich Nitride I and Silicon-rich Nitride II. Subsequently, a photoresist layer 4-104 can be deposited on the first material layer 4-102 and patterned using a photolithographic exposure and develop process, as depicted in FIG. 4-1C. Using the patterned photoresist layer 4-104 as an etch mask, the first material layer 4-102 can be etched in regions where the photoresist has been removed to form voids in the first material layer 4-102, as depicted in FIG. 4-1D. The remaining photoresist may be removed from the substrate in a cleaning step. The resulting structure of the etched first material layer 4-102 may comprise a plurality of material regions 4-106, which may be arranged, for example, in accordance to one of the single-layer structures described above in connection with FIGS. 1-3A through FIG. 1-3F. Material regions 4-106 may form columns of an optical nanostructure 1-135, for example.

In some implementations, a second material layer 4-108 (having a different refractive index than the first material layer) can be deposited on the material regions 4-106, as depicted in FIG. 4-1E. The second material layer 4-108 may be deposited by any suitable deposition process, such as PVD, PECVD, HDP PECVD, or sputtering. The second material layer 4-108 may comprise silicon oxide, silicon nitride, titanium nitride, titanium oxide, among other possible materials described above for an optical nanostructure 1-135 silicon-rich nitride materials having specific n (refractive index) and k (extinction coefficient) values such as Silicon-rich Nitride I and Silicon-rich Nitride II. In some cases, the second material layer 4-108 fills the regions between material regions 4-106. According to some implementations, the second material layer 4-108 may be planarized, for example via chemical-mechanical polishing (CMP), resulting in a planar surface as depicted in FIG. 4-1F. However, in some cases one or more layers may be deposited on the second material layer 4-108 without performing a planarization step of the second material layer 4-108. In some embodiments, the structure depicted in FIG. 4-1F may form an optical nanostructure 1-135, and be arranged, for example, in accordance to one of the single-layer structures described above in connection with FIGS. 1-3A through FIG. 1-3F.

Optionally, one or more additional layers may be added to the optical nanostructure, leading for example to the arrangement of FIG. 1-3B. FIGS. 4-1G through FIG. 4-1J depict structures associated with steps for forming a second nanostructure layer, in accordance with some embodiments. Additional layers may be formed using similar steps. In some implementations, a third material layer 4-110 can be deposited or grown on the second material layer 4-108, as depicted in FIG. 4-1G. The third material layer 4-110 may be deposited, for example, by PVD, PECVD, HDP PECVD, or sputtering. The third material layer 4-110 may include amorphous silicon, silicon nitride, titanium nitride, titanium oxide, among other possible materials described above for an optical nanostructure 1-135 silicon-rich nitride materials having specific n (refractive index) and k (extinction coefficient) values such as Silicon-rich Nitride I and Silicon-rich Nitride II. In some implementations, the third material layer 4-110 may be the same material as the first material layer 4-102. A photoresist layer 4-112 can be deposited on the third material layer 4-110 and patterned using a photolithographic exposure and develop process, according to some embodiments. Using the patterned photoresist layer 4-112 as an etch mask, the third material layer 4-110 can be etched in regions where the photoresist has been removed, as depicted in FIG. 4-1H. Residual photoresist can be removed from the substrate after etching. The resulting structure includes a plurality of material regions 4-114.

Subsequently, a fourth material layer 4-116 can be deposited on the material regions 4-114, for example via PVD, PECVD, HDP PECVD, or sputtering. In some cases, the fourth material layer 4-116 fills the regions between the material regions 4-114, as depicted in FIG. 4-1I. According to some embodiments, the fourth material layer 4-116 may be made of a material having a refractive index different from the refractive index of the third material layer 4-110. The fourth material layer 4-116 may include silicon oxide, silicon nitride, titanium nitride, titanium oxide, among other possible materials described above for an optical nanostructure 1-135 silicon-rich nitride materials having specific n (refractive index) and k (extinction coefficient) values such as Silicon-rich Nitride I and Silicon-rich Nitride II. In some cases, the fourth material layer 4-116 may be a same material as the second material layer 4-108. According to some implementations, the fourth material layer 4-116 can be planarized, for example using a CMP process step, resulting in a planar surface as depicted in FIG. 4-1J. In other implementations, one or more layers may be deposited on the fourth material layer 4-116 without planarizing the fourth material layer.

Additional examples of structures associated with another example method for fabricating an optical nanostructure are depicted in FIGS. 4-2A through FIG. 4-2J. This fabrication method is similar in some respects to the fabrication method of FIGS. 4-1A through FIG. 4-1J. Unlike the fabrication method of FIGS. 4-1A through FIG. 4-1J, however, dual mask layers 4-104/4-103 and 4-112/4-111 are used as etch masks for the formation of the material regions. Substrate 4-100 and layers 4-102, 4-104, 4-106, 4-108, 4-110, 4-112, 4-114 and 4-116 may have the same characteristics as those described in connection with FIGS. 4-1A through FIG. 4-1J. Dual mask layers (sometimes referred to as a bilayer resist) can provide improved etch selectivity or improved patterning fidelity compared to a single photoresist layer in some cases. In some embodiments, one of the mask layers (e.g., 4-103, 4-111) may comprise a so-called "hard mask" formed from a metal, oxide, nitride, or semiconductor, for example.

An example method of forming an optical nanostructure 1-135 may comprise obtaining a substrate 4-100 as depicted in FIG. 4-2A. As noted above in connection with FIG. 4-1A, the substrate may include patterned structure. A first material layer 4-102 may be deposited or grown on substrate 4-100, as described above. Additionally, a first resist layer 4-103 can be deposited on the first material layer 4-102, as depicted in FIG. 4-2B. The first resist layer 4-103 may be a hard material rather than a polymer. For example, the first resist layer 4-103 may comprise silicon oxide, silicon nitride, or tantalum, among other possible materials silicon-rich nitride materials having specific n (refractive index) and k (extinction coefficient) values such as Silicon-rich Nitride I and Silicon-rich Nitride II. According to one example, the first material layer 4-102 may be silicon nitride and the first resist layer 4-103 may be silicon oxide, though other material combinations can be used. A photoresist layer 4-104 (a second resist layer) may then be deposited on the first resist layer 4-103 and patterned using a photolithographic exposure and develop process to produce the structure depicted in FIG. 4-2C. Using the patterned photoresist layer 4-104 as a first etch mask, the first resist layer 4-103 can be etched in regions where the photoresist has been removed to transfer the pattern from the photoresist to the first resist layer 4-103, as depicted in FIG. 4-2D. During and/or after this etching step, the photoresist layer 4-104 may be removed.

Using the first resist layer 4-103 as an etch mask, the first material layer 4-102 can be etched in regions where the first resist layer 4-103 has been removed to form voids in the first material layer 4-102. The etching process leaves material regions 4-106 as depicted in FIG. 4-2E. In some cases, the remaining first resist layer 4-103 may be removed from the substrate. In other cases, the remaining first resist layer may be left on the material regions 4-106 as illustrated in FIG. 4-2E. In some cases, the first resist layer may be much thinner than the first material layer 4-102 and second material layer 4-108 and not appreciably affect performance of the optical nanostructure 4-135. In some implementations, the first resist layer 4-103 may be a same material as the second material layer 4-108. After etching to form material regions 4-106, a second material layer 4-108 can be deposited on the material regions 4-106, as depicted in FIG. 4-2F. The second material layer may fill regions between the material regions 4-106. In some cases, the second material layer 4-108 may be planarized, for example via CMP. The structure of FIG. 4-2F may form a single-layer optical nanostructure 1-135 described above in connection with FIGS. 1-3A through FIG. 1-3F.

Optionally, one or more additional layers may be added to the optical nanostructure, leading for example to the arrangement of FIG. 1-3B. FIGS. 4-2G through FIG. 4-2J depict structures associated with steps for forming a second nanostructure layer, in accordance with some embodiments. Additional layers may be formed using similar steps. For example, a third material layer 4-110 can be deposited or grown on the second material layer 4-108, as depicted in FIG. 4-2G. Subsequently, a first resist layer 4-111 can be deposited on the third material layer 4-110, and a photoresist layer 4-112 can be deposited on the first resist layer 4-111. The photoresist layer can be patterned using a photolithographic exposure and develop process. The photoresist layer 4-112 can provide an etch mask to etch the first resist layer 4-111 in regions where the photoresist has been removed, and the first resist layer can provide an etch mask to etch the third material layer 4-110, as described above and depicted in FIG. 4-2H. Residual photoresist 4-112 may be removed during or after the etching of the third material layer 4-110. Etching of the third material layer 4-110 forms material regions 4-114. A fourth material layer 4-116 can be deposited on the material regions 4-114 and may fill spaces between the material regions 4-114, as depicted in FIG. 4-2I. According to some embodiments, the fourth material layer 4-116 may be planarized, as depicted in FIG. 4-2J.

The illustrations in FIG. 4-1H and FIG. 4-2H indicate that the second material regions 4-114 are formed above the first material regions 4-106, such that bottoms of the second material regions 4-114 are spaced vertically away from tops of the first material regions 4-106 with a uniform layer of the second material layer 4-108 between these bottoms and tops. However, there may not be a space between these bottoms and tops in some implementations. For example, a planarization step of the second material layer may remove most or all of the second material layer 4-108 that is above the tops of the first material regions 4-106, so that the bottoms of the second material regions 4-114 are at essentially a same height as tops of the first material regions 4-106.

III. Example Bioanalytic Application

An example bioanalytic application is described in which an integrated semiconductor can be used to improve detection of radiation emitted from reaction chambers on a disposable chip that is used in an advanced analytical instrument. When mounted in a receptacle of the instrument, the disposable chip can be in optical and electronic communication with optical and electronic apparatus within the advanced analytic instrument. The instrument may include hardware for an external interface, so that data from the chip can be communicated to an external network. In embodiments, the term "optical" may refer to ultra-violet, visible, near-infrared, and short-wavelength infrared spectral bands. Although various types of analyses can be performed on various samples, the following explanation describes genetic sequencing. However, the invention is not limited to instruments configured for genetic sequencing.

Figures 1, 2, 3, 4, 5:
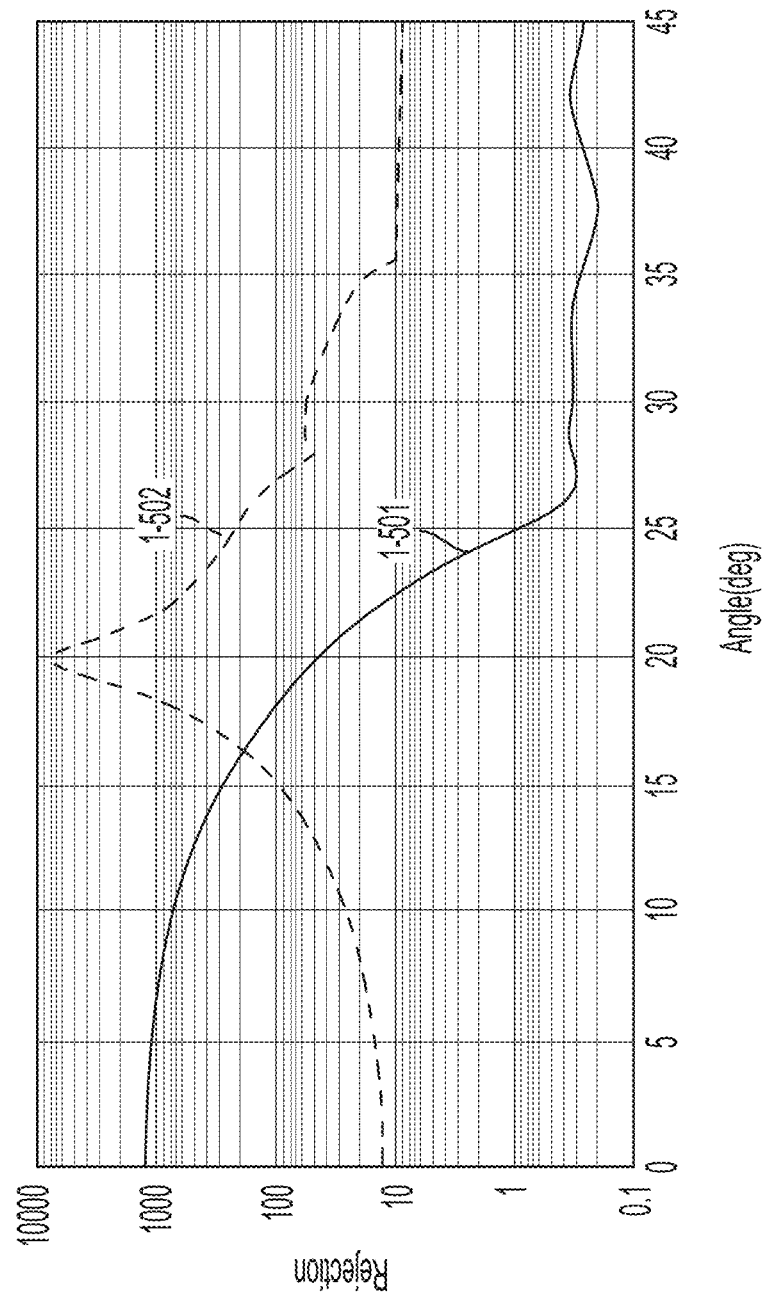
Figures 1, 2:
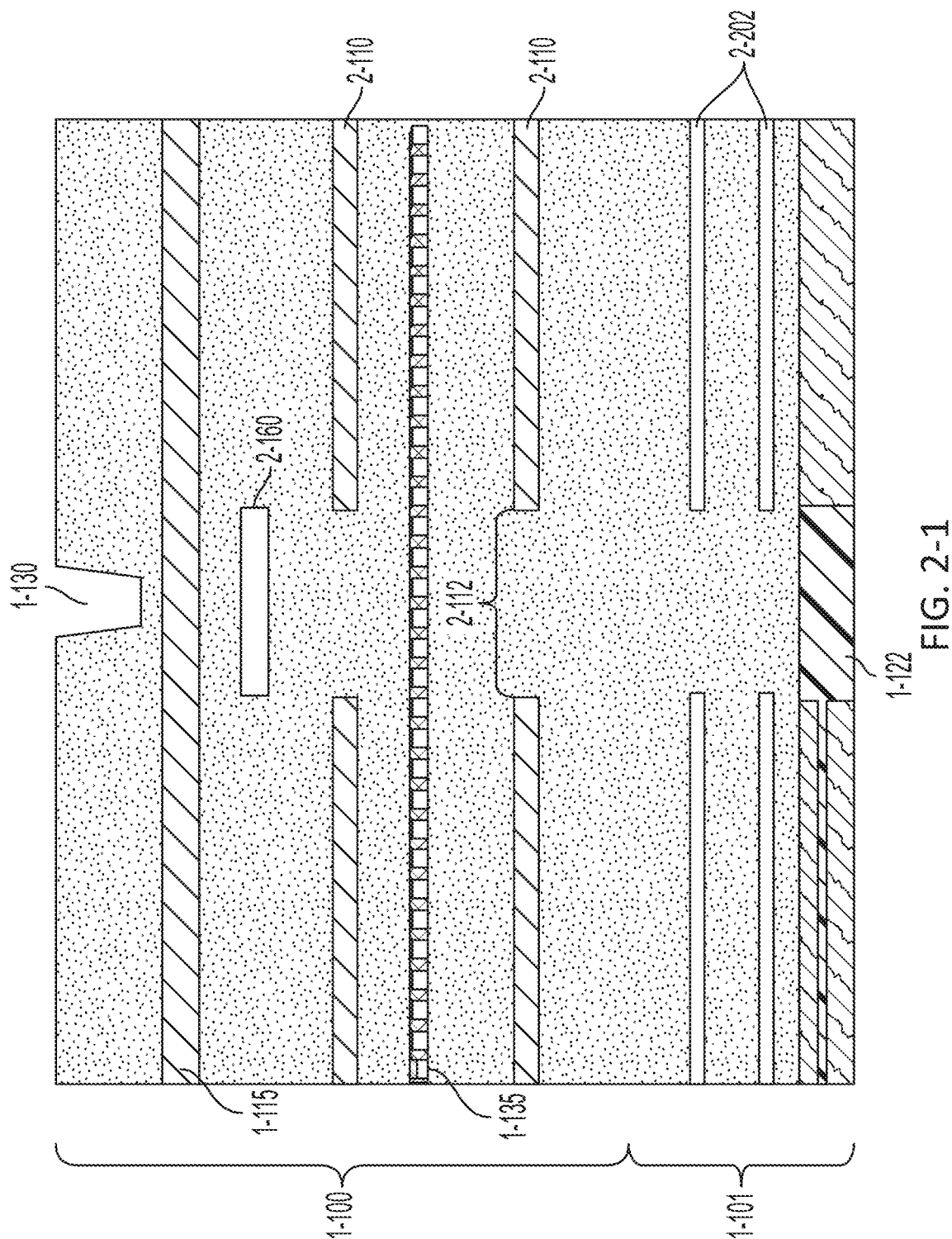
Figures 2, 3:
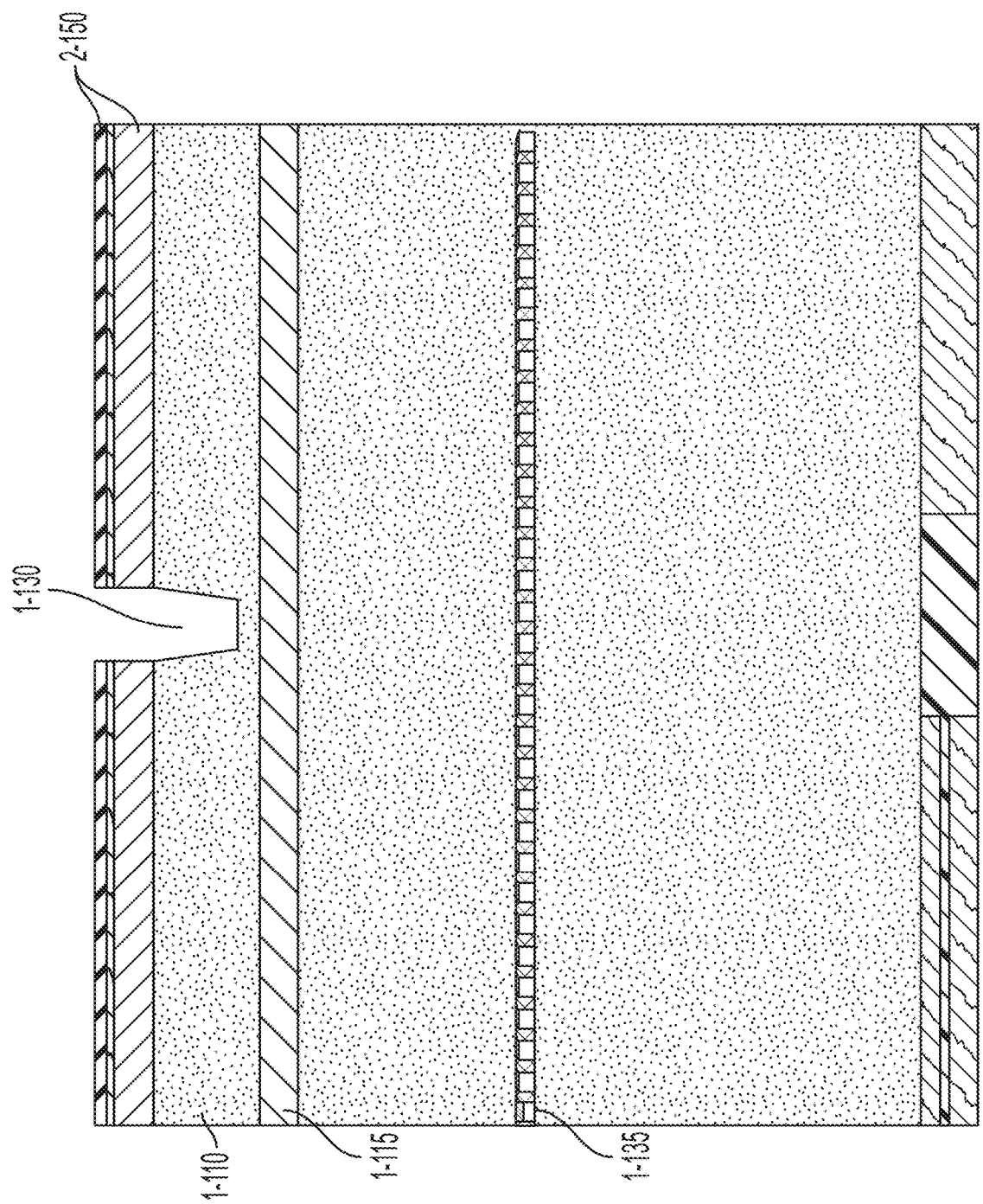
Figure 3:
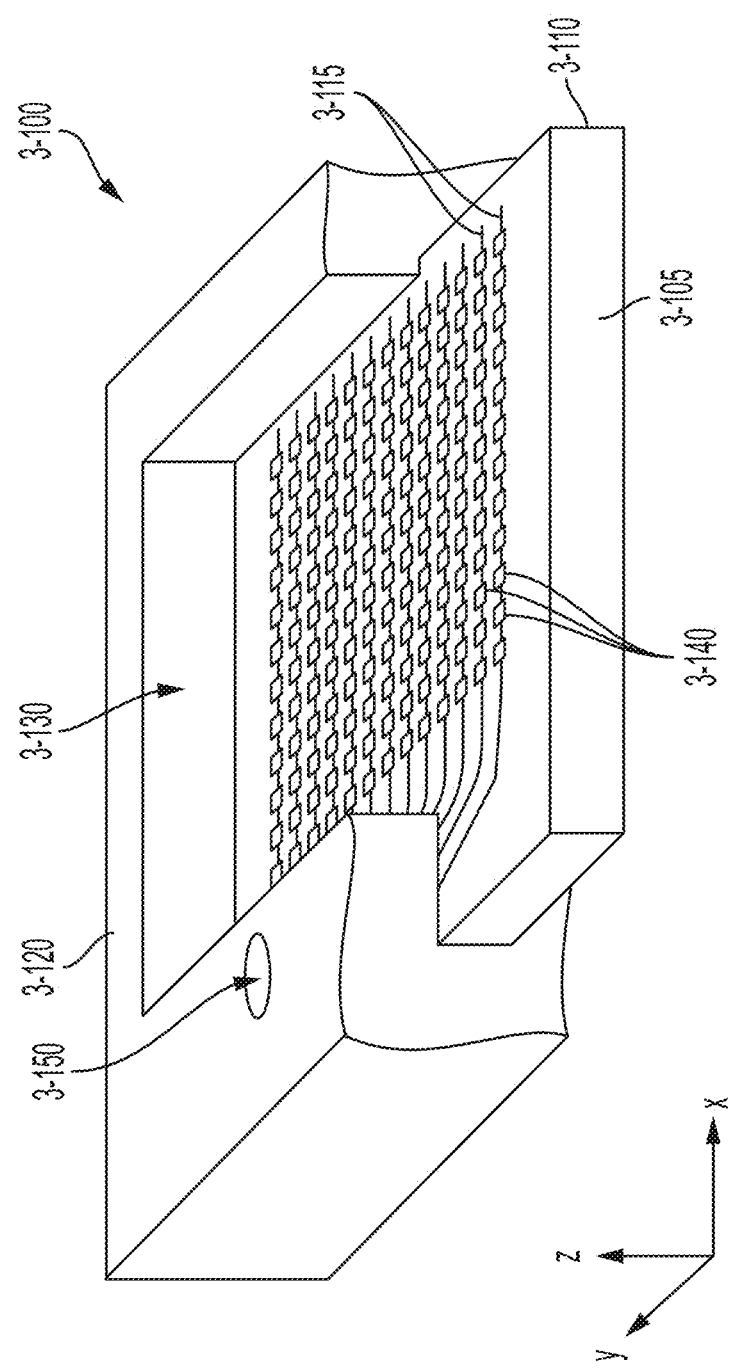

In overview and referring to FIG. 5-1A, a portable, advanced analytic instrument 5-100 can comprise one or more pulsed optical sources 5-108 mounted as a replaceable module within, or otherwise coupled to, the instrument 5-100. The portable analytic instrument 5-100 can include an optical coupling system 5-115 and an analytic system 5-160. The optical coupling system 5-115 can include some combination of optical components (which may include, for example, none, one from among, or more than one component from among the following components: lens, mirror, optical filter, attenuator, beam-steering component, beam shaping component) and be configured to operate on and/or couple output optical pulses 5-122 from the pulsed optical source 5-108 to the analytic system 5-160. The analytic system 5-160 can include a plurality of components that are arranged to direct the optical pulses to at least one reaction chamber for sample analysis, receive one or more optical signals (e.g., fluorescence, backscattered radiation) from the at least one reaction chamber, and produce one or more electrical signals representative of the received optical signals. In some embodiments, the analytic system 5-160 can include one or more photodetectors and may also include signal-processing electronics (e.g., one or more microcontrollers, one or more field-programmable gate arrays, one or more microprocessors, one or more digital signal processors, logic gates, etc.) configured to process the electrical signals from the photodetectors. The analytic system 5-160 can also include data transmission hardware configured to transmit and receive data to and from external devices (e.g., one or more external devices on a network to which the instrument 5-100 can connect via one or more data communications links). In some embodiments, the analytic system 5-160 can be configured to receive a bio-optoelectronic chip 5-140, which holds one or more samples to be analyzed.

FIG. 5-1B depicts a further detailed example of a portable analytical instrument 5-100 that includes a compact pulsed optical source 5-108. In this example, the pulsed optical source 5-108 comprises a compact, passively mode-locked laser module 5-110. A passively mode-locked laser can produce optical pulses autonomously, without the application of an external pulsed signal. In some implementations, the module can be mounted to an instrument chassis or frame 5-102, and may be located inside an outer casing of the instrument. According to some embodiments, a pulsed optical source 5-108 can include additional components that can be used to operate the optical source and operate on an output beam from the optical source 5-108. A mode-locked laser 5-110 may comprise an element (e.g., saturable absorber, acousto-optic modulator, Kerr lens) in a laser cavity, or coupled to the laser cavity, that induces phase locking of the laser's longitudinal frequency modes. The laser cavity can be defined in part by cavity end mirrors 5-111, 5-119. Such locking of the frequency modes results in pulsed operation of the laser (e.g., an intracavity pulse 5-120 bounces back-and-forth between the cavity end mirrors) and produces a stream of output optical pulses 5-122 from one end mirror 5-111 which is partially transmitting.

In some cases, the analytic instrument 5-100 is configured to receive a removable, packaged, bio-optoelectronic or optoelectronic chip 5-140 (also referred to as a "disposable chip"). The disposable chip can include a bio-optoelectronic chip 3-110, as depicted in FIG. 4 for example, that comprises a plurality of reaction chambers, integrated optical components arranged to deliver optical excitation energy to the reaction chambers, and integrated photodetectors arranged to detect fluorescent emission from the reaction chambers. In some implementations, the chip 5-140 can be disposable after a single use, whereas in other implementations the chip 5-140 can be reused two or more times. When the chip 5-140 is received by the instrument 5-100, it can be in electrical and optical communication with the pulsed optical source 5-108 and with apparatus in the analytic system 5-160.

Electrical communication may be made through electrical contacts on the chip package, for example.

In some embodiments and referring to FIG. 5-1B, the disposable chip 5-140 can be mounted (e.g., via a socket connection) on an electronic circuit board 5-130, such as a printed circuit board (PCB) that can include additional instrument electronics. For example, the PCB 5-130 can include circuitry configured to provide electrical power, one or more clock signals, and control signals to the optoelectronic chip 5-140, and signal-processing circuitry arranged to receive signals representative of fluorescent emission detected from the reaction chambers. Data returned from the optoelectronic chip can be processed in part or entirely by electronics on the instrument 5-100, although data may be transmitted via a network connection to one or more remote data processors, in some implementations. The PCB 5-130 can also include circuitry configured to receive feedback signals from the chip relating to optical coupling and power levels of the optical pulses 5-122 coupled into waveguides of the optoelectronic chip 5-140. The feedback signals can be provided to one or both of the pulsed optical source 5-108 and optical system 5-115 to control one or more parameters of the output beam of optical pulses 5-122. In some cases, the PCB 5-130 can provide or route power to the pulsed optical source 5-108 for operating the optical source and related circuitry in the optical source 5-108.

According to some embodiments, the pulsed optical source 5-108 comprises a compact mode-locked laser module 5-110. The mode-locked laser can comprise a gain medium 5-105 (which can be solid-state material in some embodiments), an output coupler 5-111, and a laser-cavity end mirror 5-119. The mode-locked laser's optical cavity can be bound by the output coupler 5-111 and end mirror 5-119. An optical axis 5-125 of the laser cavity can have one or more folds (turns) to increase the length of the laser cavity and provide a desired pulse repetition rate. The pulse repetition rate is determined by the length of the laser cavity (e.g., the time for an optical pulse to make a round-trip within the laser cavity).

In some embodiments, there can be additional optical elements (not shown in FIG. 5-1B) in the laser cavity for beam shaping, wavelength selection, and/or pulse forming. In some cases, the end mirror 5-119 comprises a saturable-absorber mirror (SAM) that induces passive mode locking of longitudinal cavity modes and results in pulsed operation of the mode-locked laser. The mode-locked laser module 5-110 can further include a pump source (e.g., a laser diode, not shown in FIG. 5-1B) for exciting the gain medium 5-105. Further details of a mode-locked laser module 5-110 can be found in U.S. patent application Ser. No. 15/844,469, titled "Compact Mode-Locked Laser Module," filed Dec. 15, 2017, which application is incorporated herein by reference.

When the laser 5-110 is mode locked, an intracavity pulse 5-120 can circulate between the end mirror 5-119 and the output coupler 5-111, and a portion of the intracavity pulse can be transmitted through the output coupler 5-111 as an output pulse 5-122. Accordingly, a train of output pulses 5-122, as depicted in the graph of FIG. 5-2, can be detected at the output coupler as the intracavity pulse 5-120 bounces back-and-forth between the output coupler 5-111 and end mirror 5-119 in the laser cavity.

FIG. 5-2 depicts temporal intensity profiles of the output pulses 5-122, though the illustration is not to scale. In some embodiments, the peak intensity values of the emitted pulses may be approximately equal, and the profiles may have a Gaussian temporal profile, though other profiles such as a $sech^2$ profile may be possible. In some cases, the pulses may not have symmetric temporal profiles and may have other temporal shapes. The duration of each pulse may be characterized by a full-width-half-maximum (FWHM) value, as indicated in FIG. 5-2. According to some embodiments of a mode-locked laser, ultrashort optical pulses can have FWHM values less than 100 picoseconds (ps). In some cases, the FWHM values can be between approximately 5 ps and approximately 30 ps.

The output pulses 5-122 can be separated by regular intervals T. For example, T can be determined by a round-trip travel time between the output coupler 5-111 and cavity end mirror 5-119. According to some embodiments, the pulse-separation interval T can be between about 1 ns and about 30 ns. In some cases, the pulse-separation interval T can be between about 5 ns and about 20 ns, corresponding to a laser-cavity length (an approximate length of the optical axis 5-125 within the laser cavity) between about 0.7 meter and about 3 meters. In embodiments, the pulse-separation interval corresponds to a round trip travel time in the laser cavity, so that a cavity length of 3 meters (round-trip distance of 6 meters) provides a pulse-separation interval T of approximately 20 ns.

According to some embodiments, a desired pulse-separation interval T and laser-cavity length can be determined by a combination of the number of reaction chambers on the chip 5-140, fluorescent emission characteristics, and the speed of data-handling circuitry for reading data from the optoelectronic chip 5-140. In embodiments, different fluorophores can be distinguished by their different fluorescent decay rates or characteristic lifetimes. Accordingly, there needs to be a sufficient pulse-separation interval T to collect adequate statistics for the selected fluorophores to distinguish between their different decay rates. Additionally, if the pulse-separation interval T is too short, the data handling circuitry cannot keep up with the large amount of data being collected by the large number of reaction chambers. Pulse-separation interval T between about 5 ns and about 20 ns is suitable for fluorophores that have decay rates up to about 2 ns and for handling data from between about 60,000 and 10,000,000 reaction chambers.

According to some implementations, a beam-steering module 5-150 can receive output pulses from the pulsed optical source 5-108 and is configured to adjust at least the position and incident angles of the optical pulses onto an optical coupler (e.g., grating coupler) of the optoelectronic chip 5-140. In some cases, the output pulses 5-122 from the pulsed optical source 5-108 can be operated on by a beam-steering module 5-150 to additionally or alternatively change a beam shape and/or beam rotation at an optical coupler on the optoelectronic chip 5-140. In some implementations, the beam-steering module 5-150 can further provide focusing and/or polarization adjustments of the beam of output pulses onto the optical coupler. One example of a beam-steering module is described in U.S. patent application Ser. No. 15/161,088 titled "Pulsed Laser and Bioanalytic System," filed May 20, 2016, which is incorporated herein by reference. Another example of a beam-steering module is described in a separate U.S. Patent Application No. 62/435,679, filed Dec. 16, 2016 and titled "Compact Beam Shaping and Steering Assembly," which is incorporated herein by reference.

Referring to FIG. 5-3, the output pulses 5-122 from a pulsed optical source can be coupled into one or more optical waveguides 5-312 on a bio-optoelectronic chip 5-140, for example. In some embodiments, the optical pulses can be coupled to one or more waveguides via a grating coupler 5-310, though coupling to an end of one or more optical waveguides on the optoelectronic chip can be used in some embodiments. According to some embodiments, a quad detector 5-320 can be located on a semiconductor substrate 5-305 (e.g., a silicon substrate) for aiding in alignment of the beam of optical pulses 5-122 to a grating coupler 5-310. The one or more waveguides 5-312 and reaction chambers or reaction chambers 5-330 can be integrated on the same semiconductor substrate with intervening dielectric layers (e.g., silicon dioxide layers) between the substrate, waveguide, reaction chambers, and photodetectors 5-322.

Each waveguide 5-312 can include a tapered portion 5-315 below the reaction chambers 5-330 to equalize optical power coupled to the reaction chambers along the waveguide. The reducing taper can force more optical energy outside the waveguide's core, increasing coupling to the reaction chambers and compensating for optical losses along the waveguide, including losses for light coupling into the reaction chambers. A second grating coupler 5-317 can be located at an end of each waveguide to direct optical energy to an integrated photodiode 5-324. The integrated photodiode can detect an amount of power coupled down a waveguide and provide a detected signal to feedback circuitry that controls the beam-steering module 5-150, for example.

The reaction chambers 5-330 or reaction chambers 5-330 can be aligned with the tapered portion 5-315 of the waveguide and recessed in a tub 5-340. There can be photodetectors 5-322 located on the semiconductor substrate 5-305 for each reaction chamber 5-330. In some embodiments, a semiconductor absorber (shown in FIG. 5-5 as an optical filter 5-530) may be located between the waveguide and a photodetector 5-322 at each pixel. A metal coating and/or multilayer coating 5-350 can be formed around the reaction chambers and above the waveguide to prevent optical excitation of fluorophores that are not in the reaction chambers (e.g., dispersed in a solution above the reaction chambers). The metal coating and/or multilayer coating 5-350 may be raised beyond edges of the tub 5-340 to reduce absorptive losses of the optical energy in the waveguide 5-312 at the input and output ends of each waveguide.

There can be a plurality of rows of waveguides, reaction chambers, and time-binning photodetectors on the optoelectronic chip 5-140. For example, there can be 128 rows, each having 512 reaction chambers, for a total of 65,536 reaction chambers in some implementations. Other implementations may include fewer or more reaction chambers, and may include other layout configurations. Optical power from the pulsed optical source 5-108 can be distributed to the multiple waveguides via one or more star couplers or multimode interference couplers, or by any other means, located between an optical coupler 5-310 to the chip 5-140 and the plurality of waveguides 5-312.

FIG. 5-4 illustrates optical energy coupling from an optical pulse 5-122 within a tapered portion of waveguide 5-315 to a reaction chamber 5-330. The drawing has been produced from an electromagnetic field simulation of the optical wave that accounts for waveguide dimensions, reaction chamber dimensions, the different materials' optical properties, and the distance of the tapered portion of waveguide 5-315 from the reaction chamber 5-330. The waveguide can be formed from silicon nitride in a surrounding medium 5-410 of silicon dioxide, for example. The waveguide, surrounding medium, and reaction chamber can be formed by microfabrication processes described in U.S. patent application Ser. No. 14/821,688, filed Aug. 7, 2015, titled "Integrated Device for Probing, Detecting and Analyzing Molecules." According to some embodiments, an evanescent optical field 5-420 couples optical energy transported by the waveguide to the reaction chamber 5-330.

A non-limiting example of a biological reaction taking place in a reaction chamber 5-330 is depicted in FIG. 5-5. The example depicts sequential incorporation of nucleotides or nucleotide analogs into a growing strand that is complementary to a target nucleic acid. The sequential incorporation can take place in a reaction chamber 5-330, and can be detected by an advanced analytic instrument to sequence DNA. The reaction chamber can have a depth between about 150 nm and about 250 nm and a diameter between about 80 nm and about 160 nm. A metallization layer 5-540 (e.g., a metallization for an electrical reference potential) can be patterned above a photodetector 5-322 to provide an aperture or iris that rejects stray radiation from adjacent reaction chambers and other unwanted light sources. According to some embodiments, polymerase 5-520 can be located within the reaction chamber 5-330 (e.g., attached to a base of the chamber). The polymerase can take up a target nucleic acid 5-510 (e.g., a portion of nucleic acid derived from DNA), and sequence a growing strand of complementary nucleic acid to produce a growing strand of DNA 5-512. Nucleotides or nucleotide analogs labeled with different fluorophores can be dispersed in a solution above and within the reaction chamber.

Figures 5, 6:
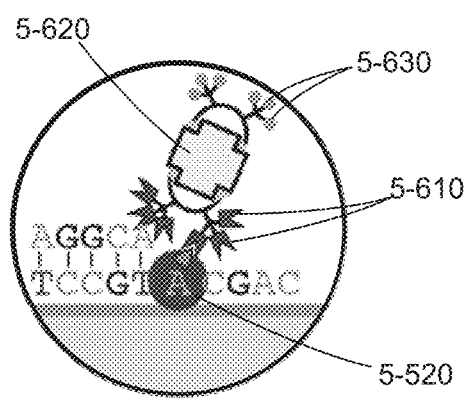

When a labeled nucleotide or nucleotide analog 5-610 is incorporated into a growing strand of complementary nucleic acid, as depicted in FIG. 5-6, one or more attached fluorophores 5-630 can be repeatedly excited by pulses of optical energy coupled into the reaction chamber 5-330 from the waveguide 5-315. In some embodiments, the fluorophore or fluorophores 5-630 can be attached to one or more nucleotides or nucleotide analogs 5-610 with any suitable linker 5-620. An incorporation event may last for a period of time up to about 100 ms. During this time, pulses of fluorescent emission resulting from excitation of the fluorophore(s) by pulses from the mode-locked laser can be detected with a time-binning photodetector 5-322, for example. In some embodiments, there can be one or more additional integrated electronic devices 5-323 at each pixel for signal handling (e.g., amplification, read-out, routing, signal preprocessing, etc.). According to some embodiments, each pixel can include at least one optical filter 5-530 (e.g., a semiconductor absorber) that passes fluorescent emission and reduces transmission of radiation from the excitation pulse. Some implementations may not use the optical filter 5-530. By attaching fluorophores with different emission characteristics (e.g., fluorescent decay rates, intensity, fluorescent wavelength) to the different nucleotides (A,C,G,T), detecting and distinguishing the different emission characteristics while the strand of DNA 5-512 incorporates a nucleic acid and enables determination of the genetic sequence of the growing strand of DNA.

Figures 5, 6, 7:
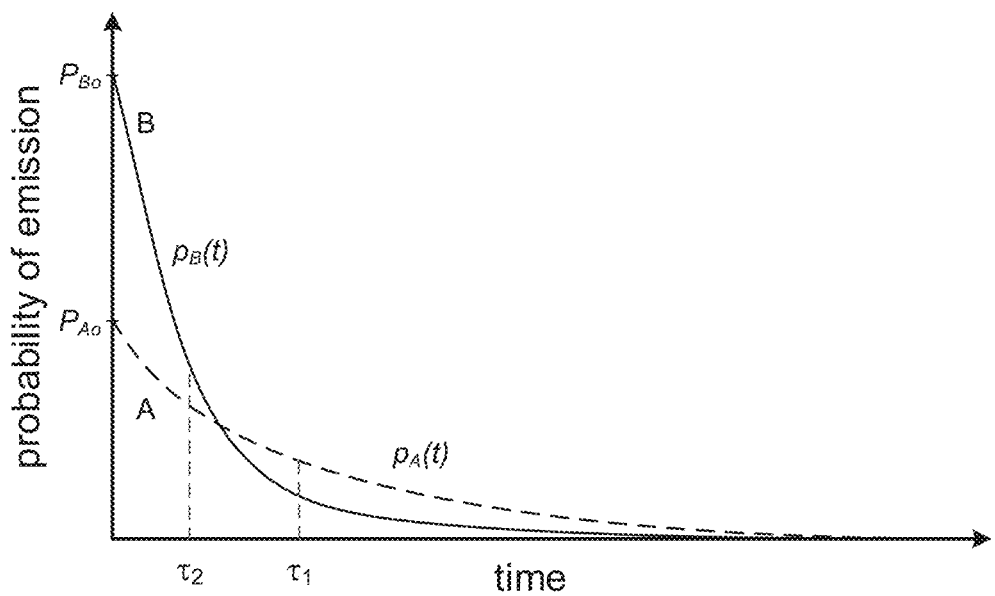
Figures 5, 6, 7, 8:
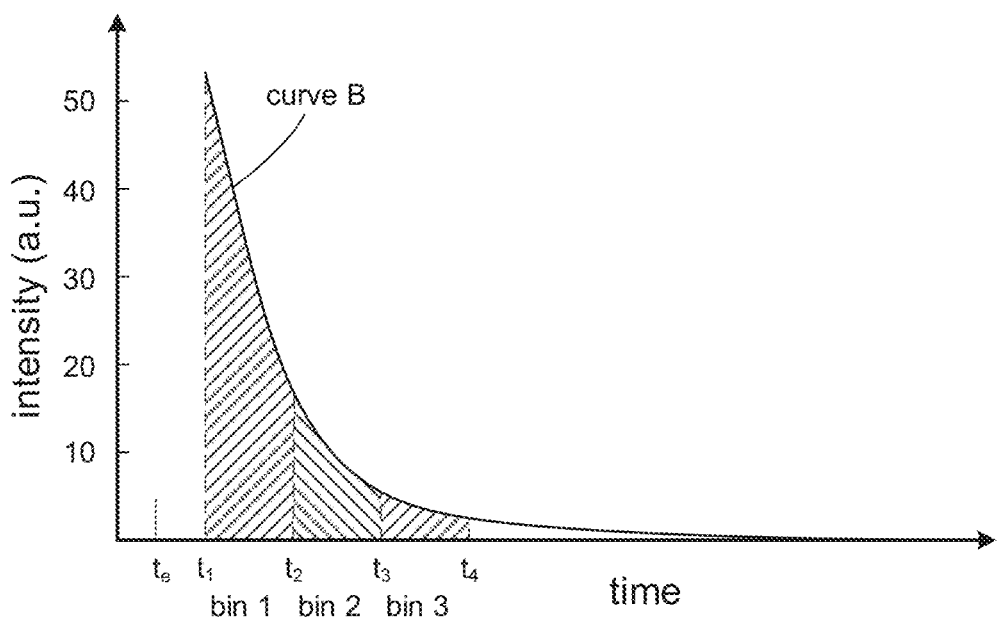
Figures 5, 6, 7, 8, 9:
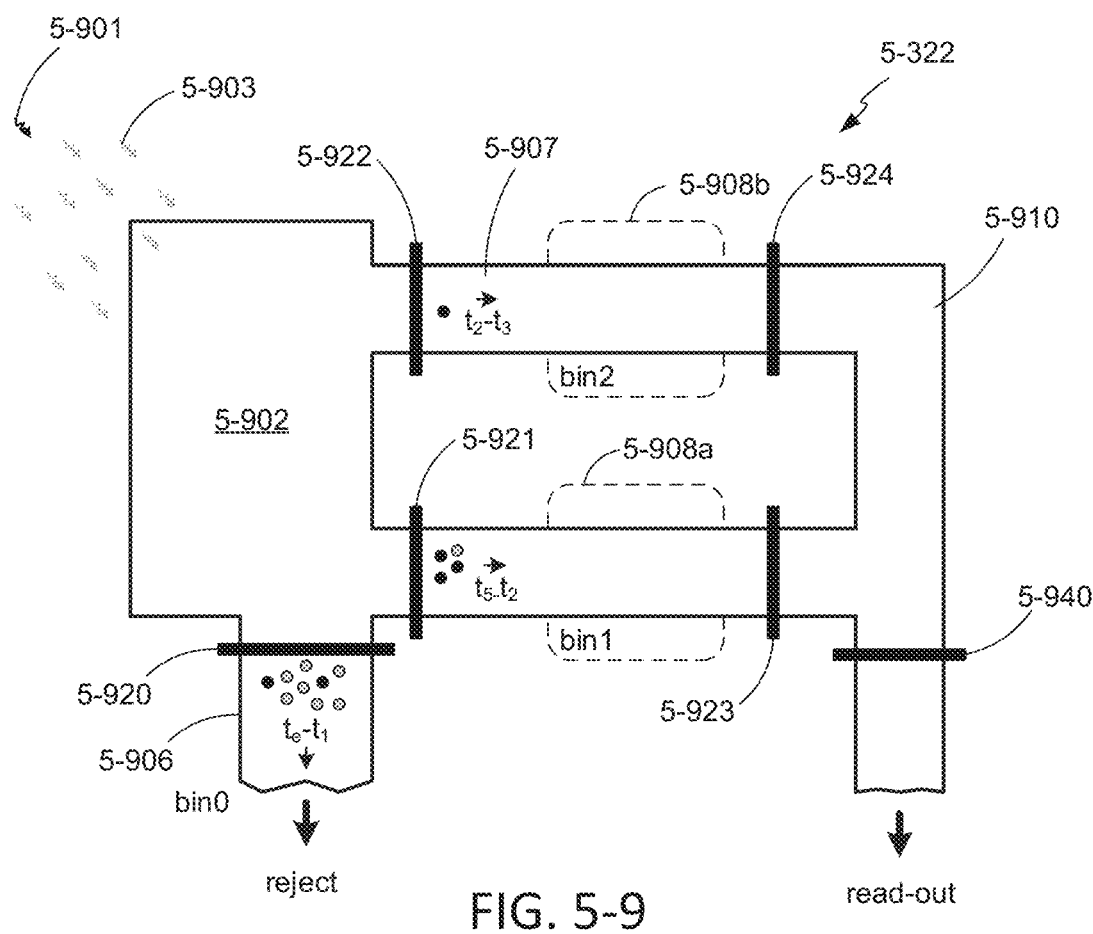
Figures 5, 6, 7, 8, 9, 10, 10A:
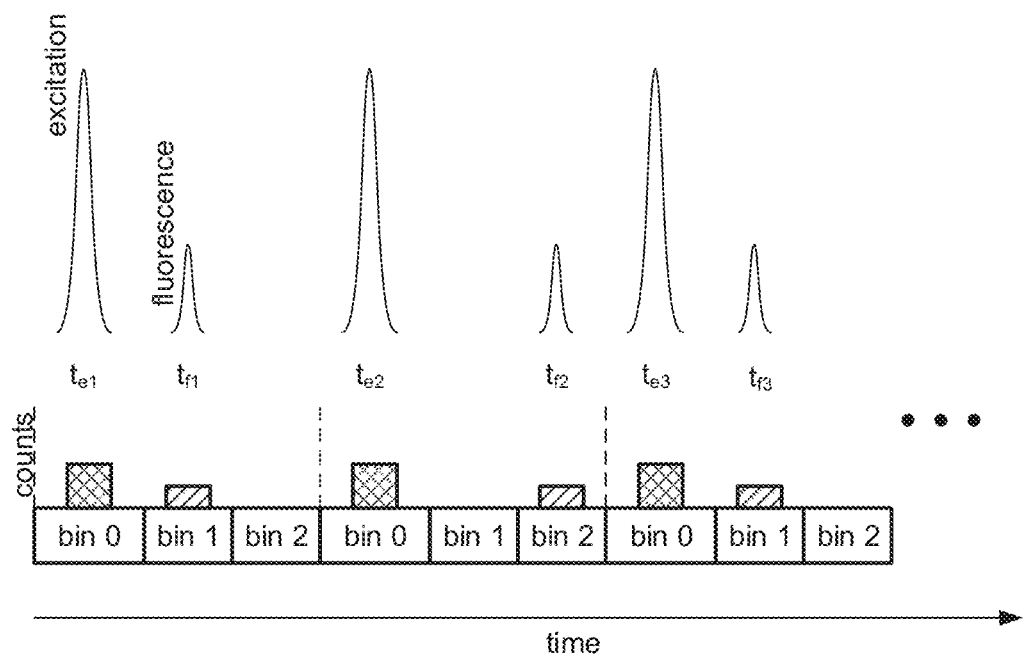
Figures 5, 6, 7, 8, 9, 10, 10B:
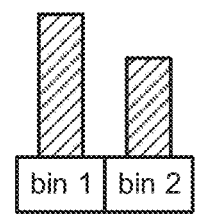
Figures 5, 6, 7, 8, 9, 10, 11, 11A:
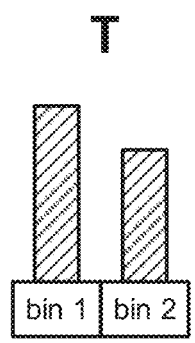
Figures 5, 6, 7, 8, 9, 10, 11, 11B:
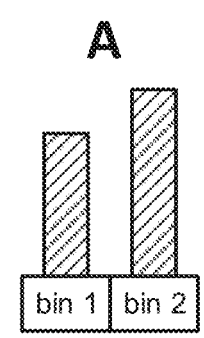
Figures 5, 6, 7, 8, 9, 10, 11, 11C:
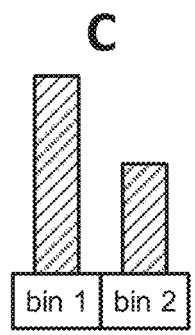
Figures 5, 6, 7, 8, 9, 10, 11, 11D:
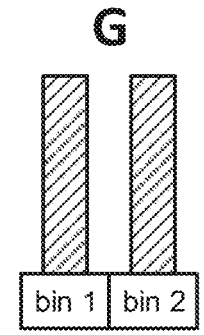
Figures 1A, 6:
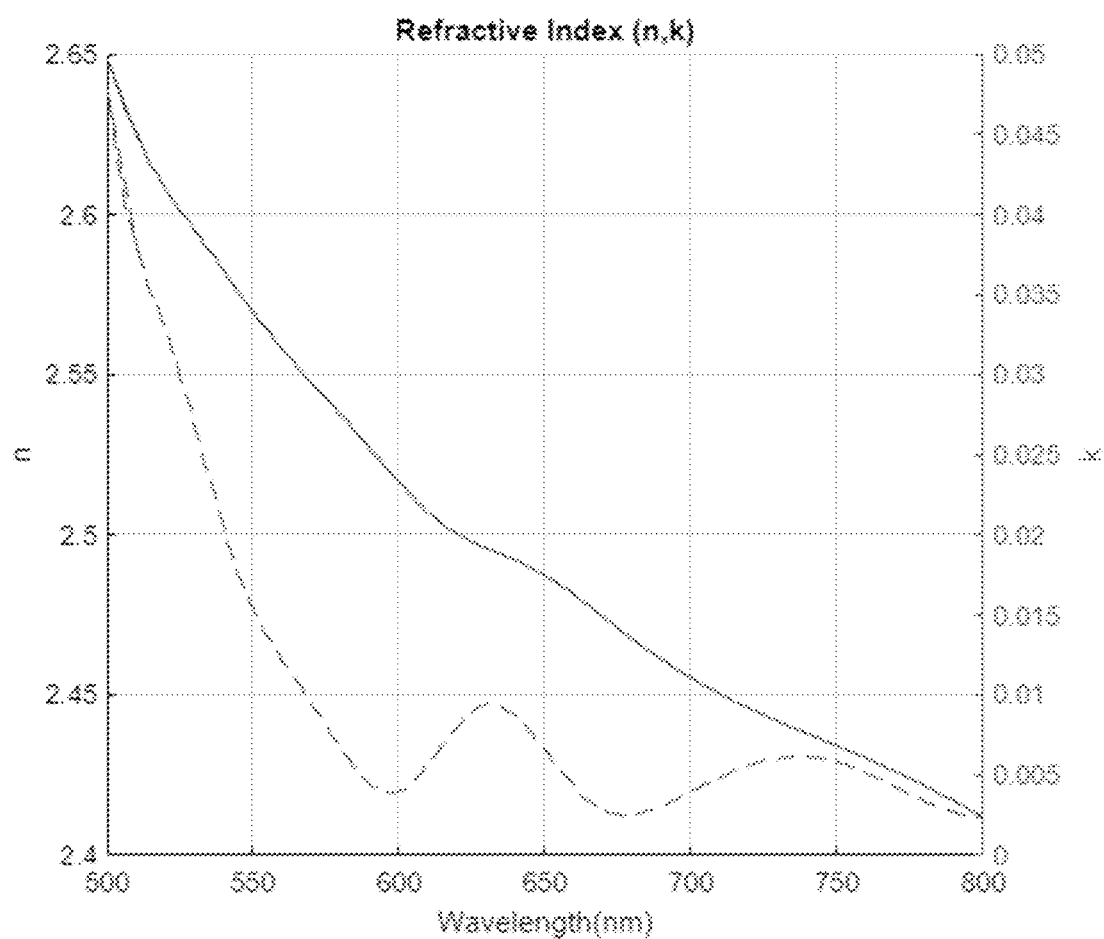
Figures 1B, 6:
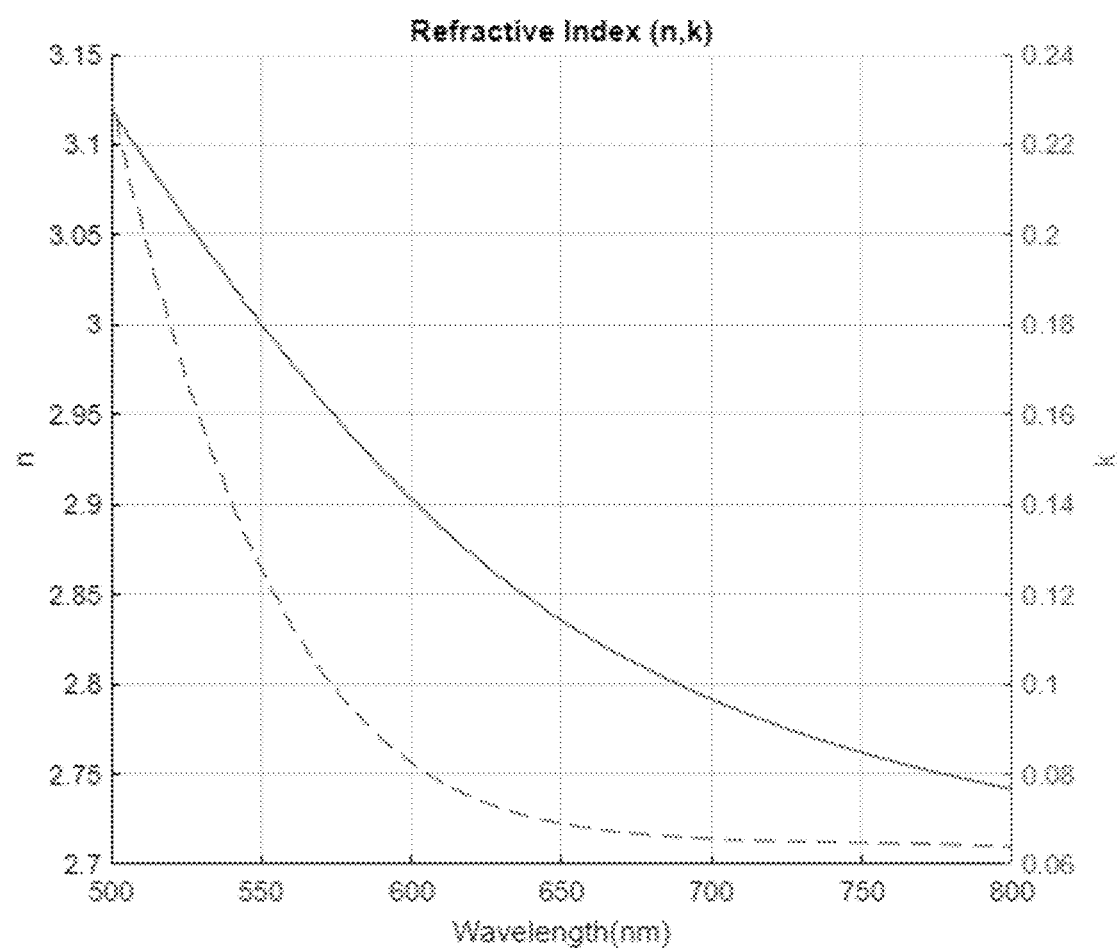

According to some embodiments, an advanced analytic instrument 5-100 that is configured to analyze samples based on fluorescent emission characteristics can detect differences in fluorescent lifetimes and/or intensities between different fluorescent molecules, and/or differences between lifetimes and/or intensities of the same fluorescent molecules in different environments. By way of explanation, FIG. 5-7 plots two different fluorescent emission probability curves (A and B), which can be representative of fluorescent emission from two different fluorescent molecules, for example. With reference to curve A (dashed line), after being excited by a short or ultrashort optical pulse, a probability $p_A(t)$ of a fluorescent emission from a first molecule may decay with time, as depicted. In some cases, the decrease in the probability of a photon being emitted over time can be represented by an exponential decay function $p_A(t) = P_{Ao}e^{-t/\tau_1}$, where $P_{Ao}$ is an initial emission probability and $\tau_1$ is a temporal parameter associated with the first fluorescent molecule that characterizes the emission decay probability. $\tau_1$ may be referred to as the "fluorescence lifetime," "emission lifetime," or "lifetime" of the first fluorescent molecule. In some cases, the value of $\tau_1$ can be altered by a local environment of the fluorescent molecule. Other fluorescent molecules can have different emission characteristics than that shown in curve A. For example, another fluorescent molecule can have a decay profile that differs from a single exponential decay, and its lifetime can be characterized by a half-life value or some other metric.

A second fluorescent molecule may have a decay profile $p_B(t)$ that is exponential, but has a measurably different lifetime $\tau_2$, as depicted for curve B in FIG. 5-7. In the example shown, the lifetime for the second fluorescent molecule of curve B is shorter than the lifetime for curve A, and the probability of emission $p_B(t)$ is higher sooner after excitation of the second molecule than for curve A. Different fluorescent molecules can have lifetimes or half-life values ranging from about 0.1 ns to about 20 ns, in some embodiments.

Differences in fluorescent emission lifetimes can be used to discern between the presence or absence of different fluorescent molecules and/or to discern between different environments or conditions to which a fluorescent molecule is subjected. In some cases, discerning fluorescent molecules based on lifetime (rather than emission wavelength, for example) can simplify aspects of an analytical instrument 5-100. As an example, wavelength-discriminating optics (such as wavelength filters, dedicated detectors for each wavelength, dedicated pulsed optical sources at different wavelengths, and/or diffractive optics) can be reduced in number or eliminated when discerning fluorescent molecules based on lifetime. In some cases, a single pulsed optical source operating at a single characteristic wavelength can be used to excite different fluorescent molecules that emit within a same wavelength region of the optical spectrum but have measurably different lifetimes. An analytic system that uses a single pulsed optical source, rather than multiple sources operating at different wavelengths, to excite and discern different fluorescent molecules emitting in a same wavelength region can be less complex to operate and maintain, more compact, and can be manufactured at lower cost.

Although analytic systems based on fluorescent lifetime analysis can have certain benefits, the amount of information obtained by an analytic system and/or detection accuracy can be increased by allowing for additional detection techniques. For example, some analytic systems 5-160 can additionally be configured to discern one or more properties of a sample based on fluorescent wavelength and/or fluorescent intensity.

Referring again to FIG. 5-7, according to some embodiments, different fluorescent lifetimes can be distinguished with a photodetector that is configured to time-bin fluorescent emission events following excitation of a fluorescent molecule. The time binning can occur during a single charge-accumulation cycle for the photodetector. A charge-accumulation cycle is an interval between read-out events during which photo-generated carriers are accumulated in bins of the time-binning photodetector. The concept of determining fluorescent lifetime by time-binning of emission events is introduced graphically in FIG. 5-8. At time $t_e$ just prior to $t_1$, a fluorescent molecule or ensemble of fluorescent molecules of a same type (e.g., the type corresponding to curve B of FIG. 5-7) is (are) excited by a short or ultrashort optical pulse. For a large ensemble of molecules, the intensity of emission can have a time profile similar to curve B, as depicted in FIG. 5-8.

For a single molecule or a small number of molecules, however, the emission of fluorescent photons occurs according to the statistics of curve B in FIG. 5-7, for this example. A time-binning photodetector 5-322 can accumulate carriers generated from emission events into discrete time bins. Three bins are indicated in FIG. 5-8, though fewer bins or more bins may be used in embodiments. The bins are temporally resolved with respect to the excitation time $t_e$ of the fluorescent molecule(s). For example, a first bin can accumulate carriers produced during an interval between times $t_1$ and $t_2$, occurring after the excitation event at time $t_e$. A second bin can accumulate carriers produced during an interval between times $t_2$ and $t_3$, and a third bin can accumulate carriers produced during an interval between times $t_3$ and $t_4$. When a large number of emission events are summed, carriers accumulated in the time bins can approximate the decaying intensity curve shown in FIG. 5-8, and the binned signals can be used to distinguish between different fluorescent molecules or different environments in which a fluorescent molecule is located.

Examples of a time-binning photodetector 5-322 are described in U.S. patent application Ser. No. 14/821,656, filed Aug. 7, 2015, titled "Integrated Device for Temporal Binning of Received Photons" and in U.S. patent application Ser. No. 15/852,571, filed Dec. 22, 2017, titled "Integrated Photodetector with Direct Binning Pixel," which are both incorporated herein by reference in their entirety. For explanation purposes, a non-limiting embodiment of a time-binning photodetector is depicted in FIG. 5-9. A single time-binning photodetector 5-322 can comprise a photon-absorption/carrier-generation region 5-902, a carrier-discharge channel 5-906, and a plurality of carrier-storage bins 5-908a, 5-908b all formed on a semiconductor substrate. Carrier-transport channels 5-907 can connect between the photon-absorption/carrier-generation region 5-902 and carrier-storage bins 5-908a, 5-908b. In the illustrated example, two carrier-storage bins are shown, but there may be more or fewer. There can be a read-out channel 5-910 connected to the carrier-storage bins. The photon-absorption/carrier-generation region 5-902, carrier-discharge channel 5-906, carrier-storage bins 5-908a, 5-908b, and read-out channel 5-910 can be formed by doping the semiconductor locally and/or forming adjacent insulating regions to provide photodetection capability, confinement, and transport of carriers. A time-binning photodetector 5-322 can also include a plurality of electrodes 5-920, 5-921, 5-922, 5-923, 5-924 formed on the substrate that are configured to generate electric fields in the device for transporting carriers through the device.

In operation, a portion of an excitation pulse 5-122 from a pulsed optical source 5-108 (e.g., a mode-locked laser) is delivered to a reaction chamber 5-330 over the time-binning photodetector 5-322. Initially, some excitation radiation photons 5-901 may arrive at the photon-absorption/carrier-generation region 5-902 and produce carriers (shown as light-shaded circles). There can also be some fluorescent emission photons 5-903 that arrive with the excitation radiation photons 5-901 and produce corresponding carriers (shown as dark-shaded circles). Initially, the number of carriers produced by the excitation radiation can too large compared to the number of carriers produced by the fluorescent emission. The initial carriers produced during a time interval $|t_e-t_1|$ can be rejected by gating them into a carrier-discharge channel 5-906 with a first electrode 5-920, for example.

At a later times mostly fluorescent emission photons 5-903 arrive at the photon-absorption/carrier-generation region 5-902 and produce carriers (indicated a dark-shaded circles) that provide useful and detectable signal that is representative of fluorescent emission from the reaction chamber 5-330. According to some detection methods, a second electrode 5-921 and third electrode 5-923 can be gated at a later time to direct carriers produced at a later time (e.g., during a second time interval $|t_1-t_2|$) to a first carrier-storage bin 5-908a. Subsequently, a fourth electrode 5-922 and fifth electrode 5-924 can be gated at a later time (e.g., during a third time interval $|t_2-t_3|$) to direct carriers to a second carrier-storage bin 5-908b. Charge accumulation can continue in this manner after excitation pulses for a large number of excitation pulses to accumulate an appreciable number of carriers and signal level in each carrier-storage bin 5-908a, 5-908b. At a later time, the signal can be read out from the bins. In some implementations, the time intervals corresponding to each storage bin are at the sub-nanosecond time scale, though longer time scales can be used in some embodiments (e.g., in embodiments where fluorophores have longer decay times).

The process of generating and time-binning carriers after an excitation event (e.g., excitation pulse from a pulsed optical source) can occur once after a single excitation pulse or be repeated multiple times after multiple excitation pulses during a single charge-accumulation cycle for the time-binning photodetector 5-322. After charge accumulation is complete, carriers can be read out of the storage bins via the read-out channel 5-910. For example, an appropriate biasing sequence can be applied to electrodes 5-923, 5-924 and at least to electrode 5-940 to remove carriers from the storage bins 5-908a, 5-908b. The charge accumulation and read-out processes can occur in a massively parallel operation on the optoelectronic chip 5-140 resulting in frames of data.

Although the described example in connection with FIG. 5-9 includes multiple charge storage bins 5-908a, 5-908b in some cases a single charge storage bin may be used instead. For example, only bin1 may be present in a time-binning photodetector 5-322. In such a case, a single storage bins 5-908a can be operated in a variable time-gated manner to look at different time intervals after different excitation events. For example, after pulses in a first series of excitation pulses, electrodes for the storage bin 5-908a can be gated to collect carriers generated during a first time interval (e.g., during the second time interval $|t_1-t_2|$), and the accumulated signal can be read out after a first predetermined number of pulses. After pulses in a subsequent series of excitation pulses at the same reaction chamber, the same electrodes for the storage bin 5-908a can be gated to collect carriers generated during a different interval (e.g., during the third time interval $|t_2-t_3|$), and the accumulated signal can be read out after a second predetermined number of pulses. Carriers could be collected during later time intervals in a similar manner if needed. In this manner, signal levels corresponding to fluorescent emission during different time periods after arrival of an excitation pulse at a reaction chamber can be produced using a single carrier-storage bin.

Regardless of how charge accumulation is carried out for different time intervals after excitation, signals that are read out can provide a histogram of bins that are representative of the fluorescent emission decay characteristics, for example. An example process is illustrated in FIG. 5-10A and FIG. 5-10B, for which two charge-storage bins are used to acquire fluorescent emission from the reaction chambers. The histogram's bins can indicate a number of photons detected during each time interval after excitation of the fluorophore(s) in a reaction chamber 5-330. In some embodiments, signals for the bins will be accumulated following a large number of excitation pulses, as depicted in FIG. 5-10A. The excitation pulses can occur at times $t_{e1}, t_{e2}, t_{e3}, \ldots t_{eN}$ which are separated by the pulse interval time T. In some cases, there can be between $10^5$ and $10^7$ excitation pulses 5-122 (or portions thereof) applied to a reaction chamber during an accumulation of signals in the electron-storage bins for a single event being observed in the reaction chamber (e.g., a single nucleotide incorporation event in DNA analysis). In some embodiments, one bin (bin 0) can be configured to detect an amplitude of excitation energy delivered with each optical pulse, and may be used as a reference signal (e.g., to normalize data). In other cases, the excitation pulse amplitude may be stable, determined one or more times during signal acquisition, and not determined after each excitation pulse so that there is no bin0 signal acquisition after each excitation pulse. In such cases, carriers produced by an excitation pulse can be rejected and dumped from the photon-absorption/carrier-generation region 5-902 as described above in connection with FIG. 5-9.

In some implementations, only a single photon may be emitted from a fluorophore following an excitation event, as depicted in FIG. 5-10A. After a first excitation event at time $t_{e1}$, the emitted photon at time $t_{f1}$ may occur within a first time interval (e.g., between times $t_1$ and $t_2$), so that the resulting electron signal is accumulated in the first electron-storage bin (contributes to bin 1). In a subsequent excitation event at time $t_{e2}$, the emitted photon at time $t_{f2}$ may occur within a second time interval (e.g., between times $t_2$ and $t_3$), so that the resulting electron signal contributes to bin 2. After a next excitation event at time tea, a photon may emit at a time $t_{f3}$ occurring within the first time interval.

In some implementations, there may not be a fluorescent photon emitted and/or detected after each excitation pulse received at a reaction chamber 5-330. In some cases, there can be as few as one fluorescent photon that is detected at a reaction chamber for every 10,000 excitation pulses delivered to the reaction chamber. One advantage of implementing a mode-locked laser 5-110 as the pulsed excitation source 5-108 is that a mode-locked laser can produce short optical pulses having high intensity and quick turn-off times at high pulse-repetition rates (e.g., between 50 MHz and 250 MHz). With such high pulse-repetition rates, the number of excitation pulses within a 10 millisecond charge-accumulation interval can be 50,000 to 250,000, so that detectable signal can be accumulated.

After a large number of excitation events and carrier accumulations, the carrier-storage bins of the time-binning photodetector 5-322 can be read out to provide a multi-valued signal (e.g., a histogram of two or more values, an N-dimensional vector, etc.) for a reaction chamber. The signal values for each bin can depend upon the decay rate of the fluorophore. For example and referring again to FIG. 5-8, a fluorophore having a decay curve B will have a higher ratio of signal in bin 1 to bin 2 than a fluorophore having a decay curve A. The values from the bins can be analyzed and compared against calibration values, and/or each other, to determine the particular fluorophore present. For a sequencing application, identifying the fluorophore can determine the nucleotide or nucleotide analog that is being incorporated into a growing strand of DNA, for example. For other applications, identifying the fluorophore can determine an identity of a molecule or specimen of interest, which may be linked to the fluorophore.

To further aid in understanding the signal analysis, the accumulated, multi-bin values can be plotted as a histogram, as depicted in FIG. 5-10B for example, or can be recorded as a vector or location in N-dimensional space. Calibration runs can be performed separately to acquire calibration values for the multi-valued signals (e.g., calibration histograms) for four different fluorophores linked to the four nucleotides or nucleotide analogs. As an example, the calibration histograms may appear as depicted in FIG. 5-11A (fluorescent label associated with the T nucleotide), FIG. 5-11B (fluorescent label associated with the A nucleotide), FIG. 5-11C (fluorescent label associated with the C nucleotide), and FIG. 5-11D (fluorescent label associated with the G nucleotide). A comparison of the measured multi-valued signal (corresponding to the histogram of FIG. 5-10B) to the calibration multi-valued signals can determine the identity "T" (FIG. 5-11A) of the nucleotide or nucleotide analog being incorporated into the growing strand of DNA.

In some implementations, fluorescent intensity can be used additionally or alternatively to distinguish between different fluorophores. For example, some fluorophores may emit at significantly different intensities or have a significant difference in their probabilities of excitation (e.g., at least a difference of about 35%) even though their decay rates may be similar. By referencing binned signals (bins 5-3) to measured excitation energy and/or other acquired signals, it can be possible to distinguish different fluorophores based on intensity levels.

In some embodiments, different numbers of fluorophores of the same type can be linked to different nucleotides or nucleotide analogs, so that the nucleotides can be identified based on fluorophore intensity. For example, two fluorophores can be linked to a first nucleotide (e.g., "C") or nucleotide analog and four or more fluorophores can be linked to a second nucleotide (e.g., "T") or nucleotide analog. Because of the different numbers of fluorophores, there may be different excitation and fluorophore emission probabilities associated with the different nucleotides. For example, there may be more emission events for the "T" nucleotide or nucleotide analog during a signal accumulation interval, so that the apparent intensity of the bins is significantly higher than for the "C" nucleotide or nucleotide analog.

Distinguishing nucleotides or any other biological or chemical specimens based on fluorophore decay rates and/or fluorophore intensities enables a simplification of the optical excitation and detection systems in an analytical instrument 5-100. For example, optical excitation can be performed with a single-wavelength source (e.g., a source producing one characteristic wavelength rather than multiple sources or a source operating at multiple different characteristic wavelengths). Additionally, wavelength discriminating optics and filters may not be needed in the detection system to distinguish between fluorophores of different wavelengths. Also, a single photodetector can be used for each reaction chamber to detect emission from different fluorophores.

The phrase "characteristic wavelength" or "wavelength" is used to refer to a central or predominant wavelength within a limited bandwidth of radiation (e.g., a central or peak wavelength within a 20 nm bandwidth output by a pulsed optical source). In some cases, "characteristic wavelength" or "wavelength" may be used to refer to a peak wavelength within a total bandwidth of radiation output by a source.

Fluorophores having emission wavelengths in a range between about 560 nm and about 900 nm can provide adequate amounts of fluorescence to be detected by a time-binning photodetector (which can be fabricated on a silicon wafer using CMOS processes). These fluorophores can be linked to biological molecules of interest, such as nucleotides or nucleotide analogs for genetic sequencing applications. Fluorescent emission in this wavelength range can be detected with higher responsivity in a silicon-based photodetector than fluorescence at longer wavelengths. Additionally, fluorophores and associated linkers in this wavelength range may not interfere with incorporation of the nucleotides or nucleotide analogs into growing strands of DNA. In some implementations, fluorophores having emission wavelengths in a range between about 560 nm and about 660 nm can be optically excited with a single-wavelength source. An example fluorophore in this range is Alexa Fluor 647, available from Thermo Fisher Scientific Inc. of Waltham, Mass.

Excitation energy at shorter wavelengths (e.g., between about 500 nm and about 650 nm) may be used to excite fluorophores that emit at wavelengths between about 560 nm and about 900 nm. In some embodiments, the time-binning photodetectors can efficiently detect longer-wavelength emission from the reaction chambers, e.g., by incorporating other materials, such as Ge, into the photodetectors' active regions.

IV. Conclusion

Having thus described several aspects of several embodiments of system architecture for an advanced analytic system 5-100, it is to be appreciated that various alterations, modifications, and improvements will readily occur to those skilled in the art. Such alterations, modifications, and improvements are intended to be part of this disclosure, and are intended to be within the spirit and scope of the invention. While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While various inventive embodiments have been described and illustrated, those of ordinary skill in the art will readily envision a variety of other means and/or structures for performing the function and/or obtaining the results and/or one or more of the advantages described, and each of such variations and/or modifications is deemed to be within the scope of the inventive embodiments described. More generally, those skilled in the art will readily appreciate that all parameters, dimensions, materials, and configurations described are meant to be examples and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure may be directed to each individual feature, system, system upgrade, and/or method described. In addition, any combination of two or more such features, systems, and/or methods, if such features, systems, system upgrade, and/or methods are not mutually inconsistent, is included within the inventive scope of the present disclosure.

Further, though some advantages of the present invention may be indicated, it should be appreciated that not every embodiment of the invention will include every described advantage. Some embodiments may not implement any features described as advantageous. Accordingly, the foregoing description and drawings are by way of example only.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used are for organizational purposes only and are not to be construed as limiting the subject matter described in any way.

Also, the technology described may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used, should be understood to control over dictionary definitions, definitions in documents incorporated by reference, and/or ordinary meanings of the defined terms.

Numerical values and ranges may be described in the specification and claims as approximate or exact values or ranges. For example, in some cases the terms "about," "approximately," and "substantially" may be used in reference to a value. Such references are intended to encompass the referenced value as well as plus and minus reasonable variations of the value. For example, a phrase "between about 10 and about 20" is intended to mean "between exactly 10 and exactly 20" in some embodiments, as well as "between 10±δ1 and 20±δ2" in some embodiments. The amount of variation δ1, δ2 for a value may be less than 5% of the value in some embodiments, less than 10% of the value in some embodiments, and yet less than 20% of the value in some embodiments. In embodiments where a large range of values is given, e.g., a range including two or more orders of magnitude, the amount of variation δ1, δ2 for a value could be as high as 50%. For example, if an operable range extends from 2 to 200, "approximately 80" may encompass values between 40 and 120 and the range may be as large as between 1 and 300. When exact values are intended, the term "exactly" is used, e.g., "between exactly 2 and exactly 200."

The term "adjacent" may refer to two elements arranged within close proximity to one another (e.g., within a distance that is less than about one-fifth of a transverse or vertical dimension of a larger of the two elements). In some cases there may be intervening structures or layers between adjacent elements. In some cases adjacent elements may be immediately adjacent to one another with no intervening structures or elements.

The indefinite articles "a" and "an," as used in the specification and in the claims, unless clearly indicated to the contrary, should be understood to mean "at least one."

The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. An integrated device comprising:
   a substrate having a first surface; and
   a plurality of pixels formed on the substrate, at least some of the plurality of pixels comprising:
   a reaction chamber configured to receive a sample;
   a sensor configured to detect emission radiation emitted from the reaction chamber;
   a waveguide configured to couple excitation radiation to the reaction chamber; and
   an optical nanostructure disposed between the waveguide and the sensor, wherein the optical nanostructure is patterned to include structural variations in a plane substantially parallel to the first surface of the substrate and reject at least a portion of the excitation radiation incident on the optical nanostructure in a direction substantially normal to the first surface.

2. The integrated device of claim 1, wherein the structural variations are periodic or quasi-periodic at least in one dimension in the plane.

3. The integrated device of claim 1, wherein the optical nanostructure exhibits a photonic bandgap.

4. The integrated device of claim 1, wherein the structural variations are periodic or quasi-periodic in two dimensions in the plane.

5. The integrated device of claim 1, wherein the structural variations exhibit a periodicity between 150 nm and 500 nm.

6. The integrated device of claim 1, wherein the optical nanostructure has no missing or significantly different periodic component within the structural variations.

7. The integrated device of claim 1, wherein the optical nanostructure comprises a first plurality of discrete regions of a dielectric material having a first refractive index.

8. The integrated device of claim 7, wherein the first plurality of discrete regions of the dielectric material exhibit a width, in the plane, between 100 nm and 300 nm.

9. The integrated device of claim 7, wherein the optical nanostructure comprises a second plurality of discrete regions of the dielectric material, the first and second discrete regions of the dielectric material being spaced from each other along a direction perpendicular to the first surface of the substrate.

10. The integrated device of claim 9, wherein the first and second discrete regions of dielectric material are staggered from each other along the direction parallel to the plane.

11. The integrated device of claim 7, wherein the first plurality of discrete regions of the dielectric material are separated by regions of a material having a second refractive index different than the first refractive index.

12. The integrated device of claim 7, wherein the first plurality of discrete regions of the dielectric material extend in a direction perpendicular to the plane.

13. The integrated device of claim 7, wherein the first plurality of discrete regions of the dielectric material exhibit a height, along the direction perpendicular to the first surface of the substrate, between 100 nm and 300 nm.

14. The integrated device of claim 1, further comprising an iris disposed between the reaction chamber and the sensor.

15. The integrated device of claim 1, further comprising an optical element disposed between the reaction chamber and the sensor that increases a concentration of the emission radiation onto the sensor.

16. The integrated device of claim 15, wherein the optical element comprises a disk of dielectric material having, for a same wavelength of the emission radiation, a first index of refraction that is different from a second index of refraction for material surrounding the disk.

17. A method of operating an integrated device, the method comprising:
    coupling, from a waveguide formed on a substrate, excitation radiation to a reaction chamber formed adjacent to the waveguide, the excitation radiation having a first wavelength;
    passing emission radiation from the reaction chamber through an optical nanostructure to a sensor, wherein the emission radiation has a second wavelength different than the first wavelength and is generated in response to excitation of at least one emitter in the reaction chamber by the excitation radiation; and
    rejecting at least a portion of the excitation radiation with the optical nanostructure.

18. The method of claim 17, further comprising detecting at least a portion of the emission radiation which passes through the optical nanostructure with a sensor formed on the substrate.

19. The method of claim 17, wherein rejecting a portion of the excitation radiation comprises causing the portion of the excitation radiation to reflect from the optical nanostructure.

20. The method of claim 17, wherein the first wavelength is within a photonic bandgap of the optical nanostructure.

21. The method of claim 17, wherein the second wavelength is outside the photonic bandgap of the optical nanostructure.

22. The method of claim 17, wherein the structural variations are periodic or quasi-periodic at least in one dimension in the plane.

23. The method of claim 17, wherein the structural variations are periodic or quasi-periodic in two dimensions in the plane.

24. The method of claim 17, further comprising passing the emission radiation from the reaction chamber through an iris.

25. The method of claim 17, further comprising rejecting the excitation radiation with the iris.

26. The method of claim 17, further comprising concentrating the emission radiation with a dielectric disk located between the reaction chamber and optical nanostructure.

27. A method for fabricating an integrated device, the method comprising:
    forming, on a substrate having a first surface, a plurality of pixels such that at least some of the plurality of pixels comprises a reaction chamber and a sensor;
    forming a waveguide in the at least some of the plurality of pixels; and
    forming an optical nanostructure in the at least some of the plurality of pixels between the waveguide and the sensor, wherein forming the optical nanostructure comprises:
    patterning a first dielectric material to include structural variations in a plane substantially parallel to the first surface of the substrate.

28. The method of claim 27, wherein patterning a first dielectric material comprises forming periodic or quasi-periodic patterns in the first dielectric material.

29. The method of claim 27, wherein patterning the first dielectric material to include structural variations comprises etching the first dielectric material to form voids in the first dielectric material.

30. The method of claim 29, further comprising filling the voids with a second dielectric material different than the first dielectric material.

\* \* \* \* \*